US010631818B2

United States Patent
Vogelsang et al.

(10) Patent No.: US 10,631,818 B2
(45) Date of Patent: Apr. 28, 2020

(54) MOBILE RADIOGRAPHY CALIBRATION FOR TOMOSYNTHESIS USING EPIPOLAR GEOMETRY

(71) Applicant: CARESTREAM HEALTH, INC., Rochester, NY (US)

(72) Inventors: Levon O. Vogelsang, Webster, NY (US); Lawrence A. Ray, Rochester, NY (US); Richard A. Simon, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 180 days.

(21) Appl. No.: 16/028,935

(22) Filed: Jul. 6, 2018

(65) Prior Publication Data

US 2019/0175136 A1    Jun. 13, 2019

Related U.S. Application Data

(60) Provisional application No. 62/598,000, filed on Dec. 13, 2017.

(51) Int. Cl.
| | |
|---|---|
| *B41M 5/00* | (2006.01) |
| *G06K 9/00* | (2006.01) |
| *A61B 6/00* | (2006.01) |
| *G06T 11/00* | (2006.01) |

(52) U.S. Cl.
CPC ............ *A61B 6/582* (2013.01); *A61B 6/4405* (2013.01); *A61B 6/52* (2013.01); *G06T 11/005* (2013.01)

(58) Field of Classification Search
USPC ....... 382/100, 103, 106, 128–133, 154, 168, 382/181, 189, 199, 219, 232, 254, 274, 382/276, 285–295, 305, 107, 312; 600/431; 378/4, 21, 28
See application file for complete search history.

(56) References Cited

U.S. PATENT DOCUMENTS

| 7,031,497 | B2 | 4/2006 | Trajković | |
|---|---|---|---|---|
| 2003/0086590 | A1* | 5/2003 | Trajkovic | G06T 7/246 382/107 |
| 2004/0161137 | A1* | 8/2004 | Aben | A61B 6/583 382/128 |
| 2013/0051516 | A1* | 2/2013 | Yang | A61B 6/03 378/4 |
| 2015/0342551 | A1* | 12/2015 | Lavi | A61B 6/504 600/431 |
| 2017/0020481 | A1* | 1/2017 | Hawker | A61B 6/583 |

* cited by examiner

*Primary Examiner* — Seyed H Azarian

(57) ABSTRACT

A method for geometric calibration of a mobile radiography apparatus, executed at least in part by a computer, acquires a series of tomosynthesis projection images of a patient positioned between an x-ray source of the mobile radiography apparatus and a detector that is positionally uncoupled from the x-ray source. A vector field is generated having a first set of vectors indicative of feature movement between a first acquired projection image and a second acquired projection image. The generated vector field is associated with an epipolar geometry according to an optimization of an energy relationship between an epipolar model and the generated vector field values. The mobile radiography apparatus is calibrated according to the associated model epipolar geometry. At least a portion of the tomosynthesis image is reconstructed and displayed.

11 Claims, 29 Drawing Sheets

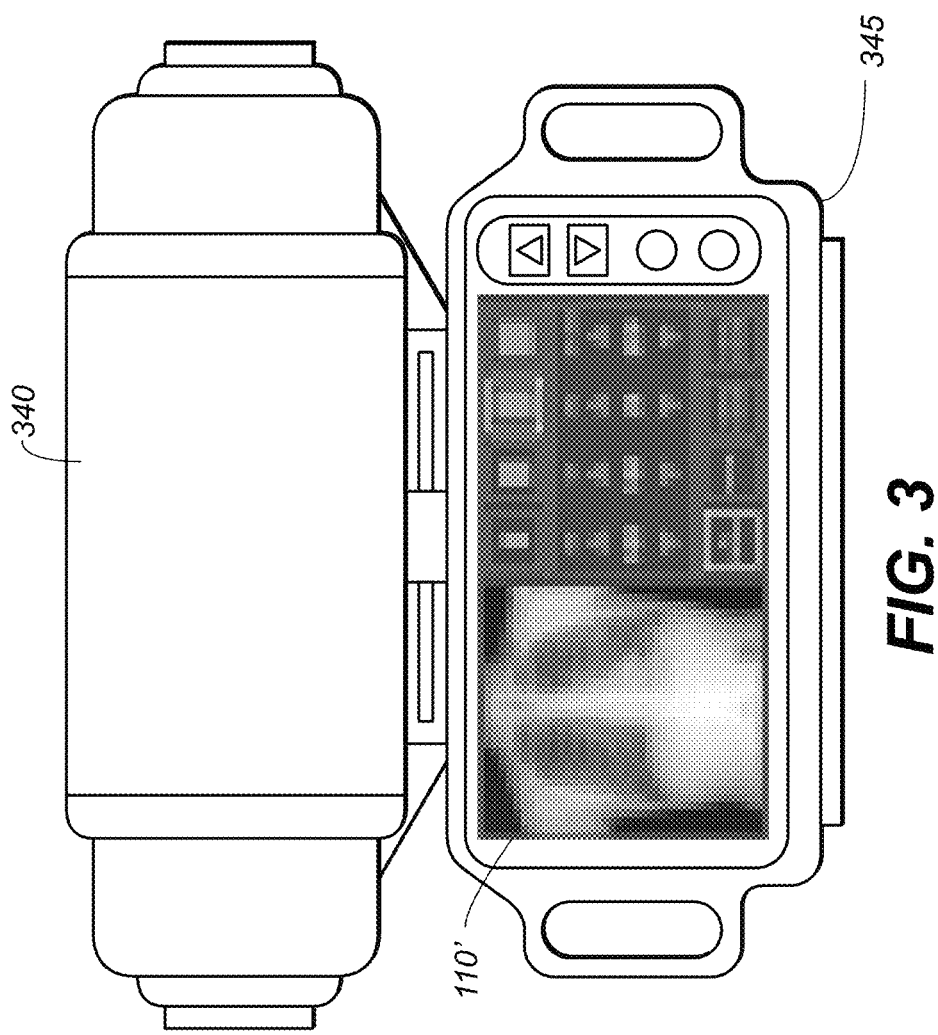

| Patient Name | Location | Exam | Exam Time |
|---|---|---|---|
| James Johnson | Rm 203 | Portable Chest | 4/11/2010 11:23:51 AM |
| Fred Smith | Rm 224 | Knee | 4/11/2010 11:24:12 AM |
| Fred Jones | Rm 245 | Portable Chest | 4/11/2010 11:23:44 AM |
| Scott Smith | Rm 252 | Portable Hip | 4/11/2010 11:24:05 AM |
| John Jones | Rm 483 | Portable Hip | 4/11/2010 11:22:48 AM |
| Bill Miller | Rm 508 | Portable Hip | 4/11/2010 11:23:37 AM |
| Bill Smith | Rm 572 | Knee | 4/11/2010 11:23:30 AM |
| Bill Miller | Rm 778 | Portable Chest | 4/11/2010 11:23:16 AM |
| Mike Jones | Rm 884 | Knee | 4/11/2010 11:23:23 AM |
| Robert Jones | Rm 944 | Portable Hip | 4/11/2010 11:23:02 AM |
| Fred Johnson | Rm 993 | Knee | 4/11/2010 11:23:58 AM |

New Exam Requested
Exam Time: 4/11/2010 11:25:01 AM
Routine
Location: Rm 816
Patient Name: Mark Bailey
Exam: Portable Hip 110, 110'

FIG. 6

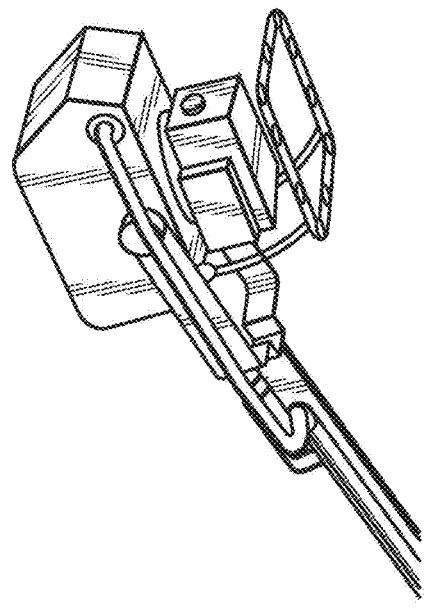
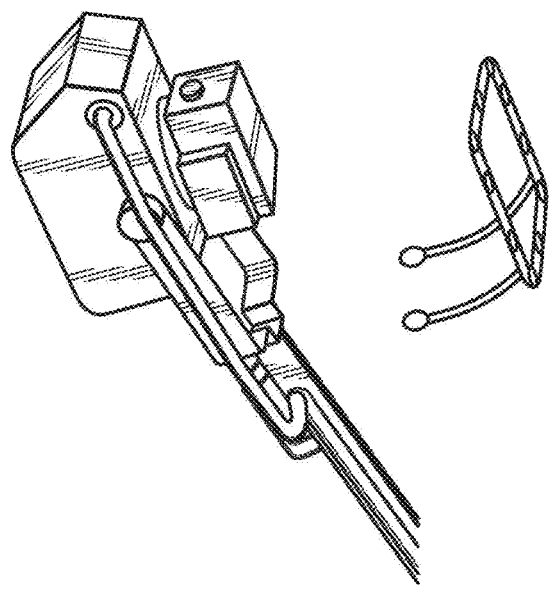
FIG. 19

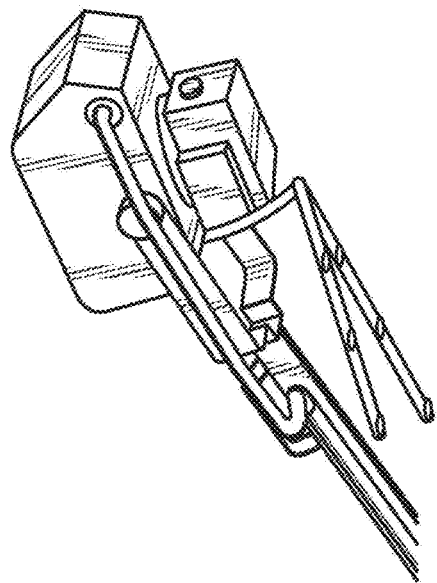
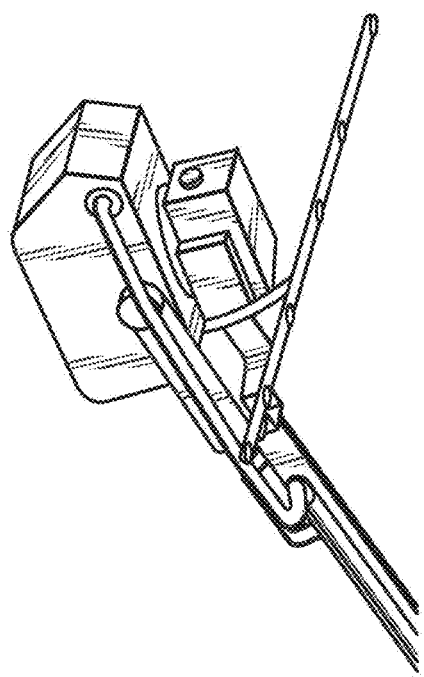
FIG. 20

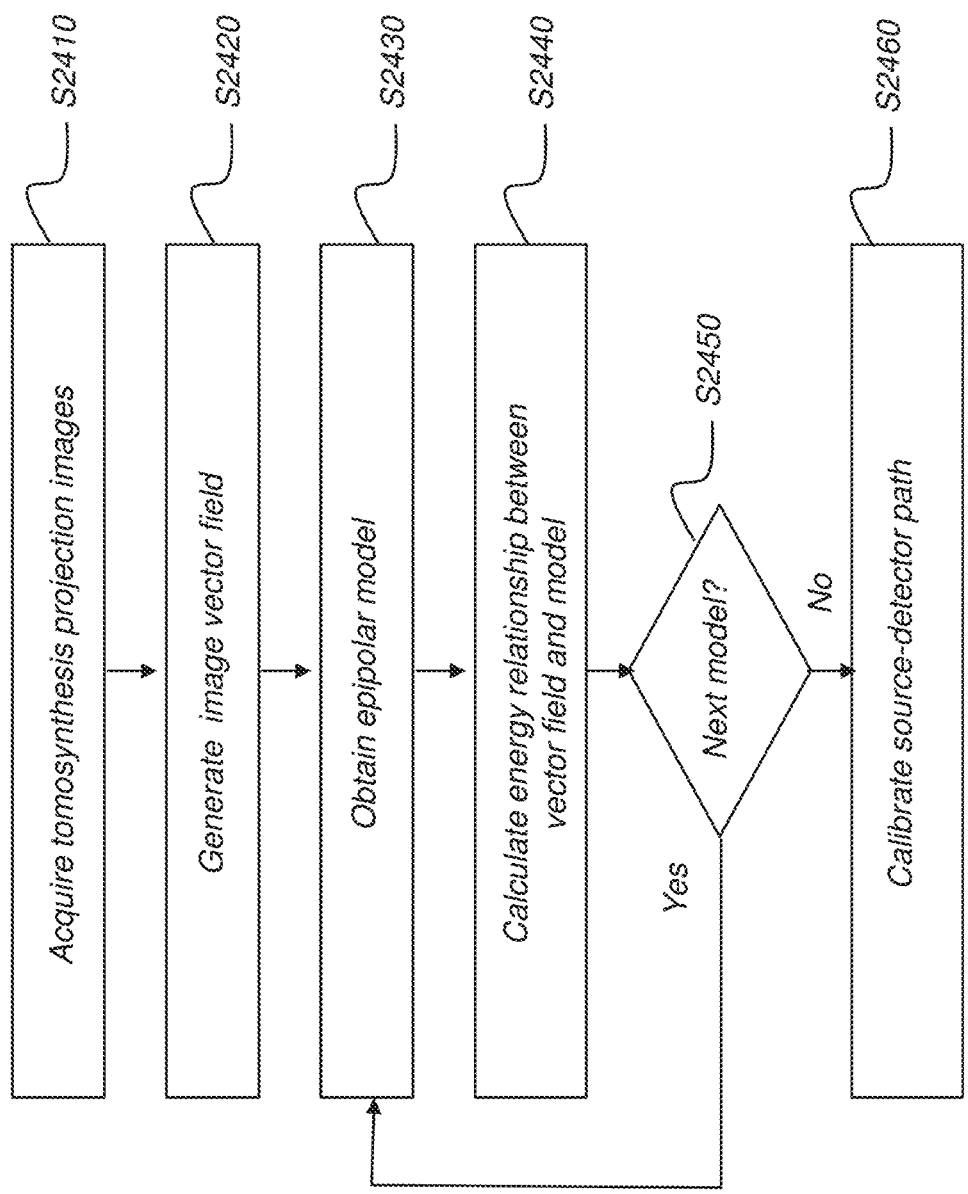

MOBILE RADIOGRAPHY CALIBRATION FOR TOMOSYNTHESIS USING EPIPOLAR GEOMETRY

CROSS REFERENCE TO RELATED APPLICATIONS

This application claims priority to U.S. Provisional application U.S. Ser. No. 62/598,000, filed on Dec. 13, 2017, entitled "MOBILE RADIOGRAPHY CALIBRATION FOR TOMOSYNTHESIS USING EPIPOLAR GEOMETRY", in the names of Vogelsang et al, incorporated herein in its entirety.

TECHNICAL FIELD

The disclosure relates generally to the field of medical imaging, and in particular to radiographic imaging apparatus. More specifically, the disclosure relates to a mobile radiography apparatus having additional tomosynthesis capability.

BACKGROUND

Digital X-ray tomosynthesis is an imaging technique that enables three-dimensional imaging of a patient using a large-area digital detector typically used for conventional (single projection) radiography. A finite number of projection images over a limited angular range, typically between 20° and 40°, are acquired by varying the orientations of the x-ray tube, patient and detector. This is usually accomplished by either moving both the detector and x-ray source or by fixing the position of the detector (source) and moving the x-ray source (detector). In applications where the detector is fixed, multiple spatially distributed X-ray sources may alternately be used, or movable sources may be displaced in various patterns or trajectories. Three-dimensional data is reconstructed from the captured projections in the form of a number of slices through the patient anatomy, each parallel to the detector plane. A consequence of limited angular scanning is that the in depth resolution is much lower than the in-plane resolution of the reconstructed object.

Reconstruction of volumetric data from a tomosynthesis system requires knowledge of the underlying capture geometry, including the relative orientation and position of the detector, the movement and position of the source for each projection, and potential patient motion. In a standard tomosynthesis apparatus, many of the geometric variables are well known, as the detector position is precisely specified, and the relationship between source and detector is mechanically fixed and well established.

For a bed-side portable tomosynthesis system, however, the capture geometry can be difficult to determine with the desired accuracy. Detector positioning is done by the operator with consideration for affording the patient a reasonable degree of comfort, but without a high degree of geometric precision. The detector is placed behind a patient by an attending operator, so that often the detector is completely obscured by the patient's body. For instance the patient may be in a propped position, with the detector placed behind the patient. The angle between the detector plane and a horizontal plane is only approximately known. Moreover, the detector might be skewed with respect to the transport path of the x-ray source, which further complicates the reconstruction process. The result is that the image quality of the resulting volumetric data can be compromised.

There is a need for a calibration utility that overcomes the limitations aforementioned and more accurately defines the geometry of the tomosynthesis system when using mobile radiography apparatus.

SUMMARY

An aspect of this application is to advance the art of radiography tomosynthesis systems.

Another aspect of this application to address in whole or in part, at least the foregoing noted problems and other deficiencies in the related art.

It is another aspect of this application to provide in whole or in part, at least the advantages described herein.

Another aspect of the application is to provide methods and/or apparatus by which mobile radiography carts can additionally include tomosynthesis capabilities.

Another aspect of the application is to provide methods and/or apparatus embodiments by which mobile radiography carts can acquire projection images and generate reconstructed three-dimensional tomosynthesis images.

Another aspect of the application is to provide methods and/or apparatus embodiments by which mobile radiography carts can acquire x-ray tomosynthesis projection images and generate the reconstruction of two-dimensional or three-dimensional tomosynthesis images where an imaging geometry of x-ray source positions relative to a radiographic detection array is not known for the plurality of x-ray tomosynthesis projection images.

These objects are given only by way of illustrative example, and such objects may be exemplary of one or more embodiments of the invention. Other desirable objectives and advantages inherently achieved may become apparent to those skilled in the art. The invention is defined by the appended claims.

According to one aspect of the disclosure, there is provided a method for geometric calibration of a mobile radiography apparatus, the method executed at least in part by a computer and comprising: a) acquiring a series of tomosynthesis projection images of a patient positioned between an x-ray source of the mobile radiography apparatus and a detector that is positionally uncoupled from the x-ray source; b) generating a vector field having a first set of vectors indicative of feature movement between a first acquired projection image and a second acquired projection image; c) associating the generated vector field with an epipolar geometry according to an optimization of an energy relationship between an epipolar model and the generated vector field values; d) calibrating the mobile radiography apparatus according to the associated model epipolar geometry; and e) reconstructing and displaying at least a portion of the tomosynthesis image according to the calibration.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 3 is a diagram showing an exemplary embodiment of a display/monitor as a second display mounted to a boom assembly of a mobile radiography unit according to the present disclosure.

FIG. 4 is a diagram that illustrates an embodiment of a sign-on screen according to the present disclosure.

FIGS. 5-8 are diagrams that illustrate exemplary functions implemented at embodiments of a mobile x-ray imaging apparatus.

FIGS. 19-20 are diagrams that show mobile radiographic imaging systems that can include first and second (e.g., multiple) radiographic x-ray sources according to embodiments of the present disclosure.

FIG. 24 is a logic flow diagram showing a portion of the processing used for model selection and calibration.

DETAILED DESCRIPTION OF THE EMBODIMENTS

Figure 1:
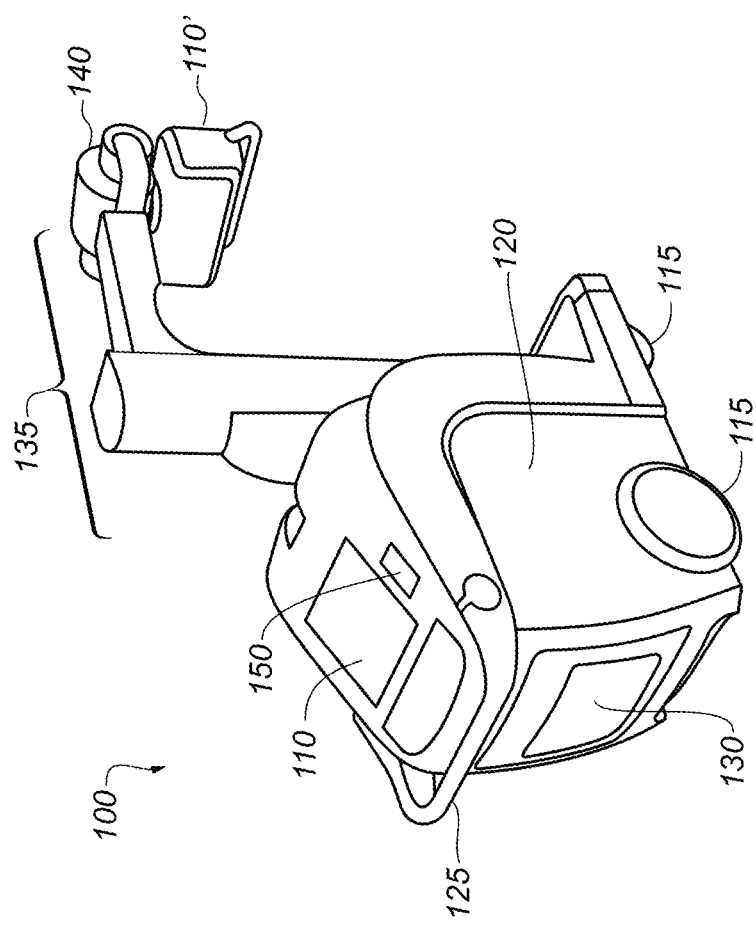
FIG. 1 is a diagram showing a perspective view of a mobile radiography unit that can use portable radiographic detectors or flat panel detectors according to embodiments of the present disclosure.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

In this document, the terms "a" or "an" are used, as is common in patent documents, to include one or more than one, independent of any other instances or usages of "at least one" or "one or more". In this document, the term "or" is used to refer to a nonexclusive or, such that "A or B" includes "A but not B", "B but not A", and "A and B", unless otherwise indicated. In this document, the terms "including" and "in which" are used as the plain-English equivalents of the respective terms "comprising" and "wherein". Also, in the following claims, the terms "including" and "comprising" are open-ended, that is, a system, device, article, or process that includes elements in addition to those listed after such a term in a claim are still deemed to fall within the scope of that claim.

Portable radiographic systems are routinely used in hospitals. Compared to standard projection radiography, tomosynthesis provides improved depiction of fine details not visible in normal radiographs due to overlying structures. These benefits provide the impetus to develop portable tomosynthesis systems that can be utilized in the intensive care unit, emergency department, and operating rooms where moving the patient is either impracticable or ill-advised due to the risk of harm to the patient.

The image quality of the reconstruction depends, in part, upon accurate knowledge of the acquisition scan geometry, the relative position of the x-ray source and detector for each projection. Uncertainties in the scan geometry can lead to artifacts and/or blurring in the reconstructed object. The development of portable tomosynthesis systems has been hampered by difficulties in accurately determining the acquisition scan geometry. There remains a need for improved X-ray tomosynthesis systems that can be made portable and still provide reliable clinical images and data.

FIG. 1 is a diagram showing a perspective view of a mobile radiography apparatus 100 that can use portable radiographic detectors or flat panel detectors according to embodiments of the application. The exemplary mobile x-ray or radiographic apparatus 100 of FIG. 1 can be employed for digital radiography (DR) and/or tomosynthesis. As shown in FIG. 1, mobile radiography apparatus 100 can include a moveable transport frame 120 that includes a first display 110 and an optional second display 110' to display relevant information such as obtained images and related data. The second display 110' can be pivotable mounted at the x-ray source 140 to be viewable/touchable from a 360 degree area.

The displays 110, 110' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s). An optional touchpad 150 allows functions such as operator identification.

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography cassettes. The area/holder can be storage area 130 (e.g., disposed on the frame 120) configured to removably retain at least one digital radiography (DR) detector. The storage area 130 can be configured to hold a plurality of detectors and can also be configured to hold one size or multiple sizes of DR detectors.

Mounted to frame 120 is a support column 135 that supports an x-ray source 140, also called an x-ray tube, tube head, or generator that can be mounted to the support member 135. In the embodiment shown in FIG. 1, the support member (e.g., column 135) can include a second section that extends outward a fixed/variable distance from a first section where the second section is configured to ride vertically up and down the first section to the desired height for obtaining the image. In addition, the support column is rotatably attached to the moveable frame 120. In another embodiment, the tube head or x-ray source 140 can be rotatably coupled to the support column 135. In another exemplary embodiment, an articulated member of the support column that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions.

Figure 2:
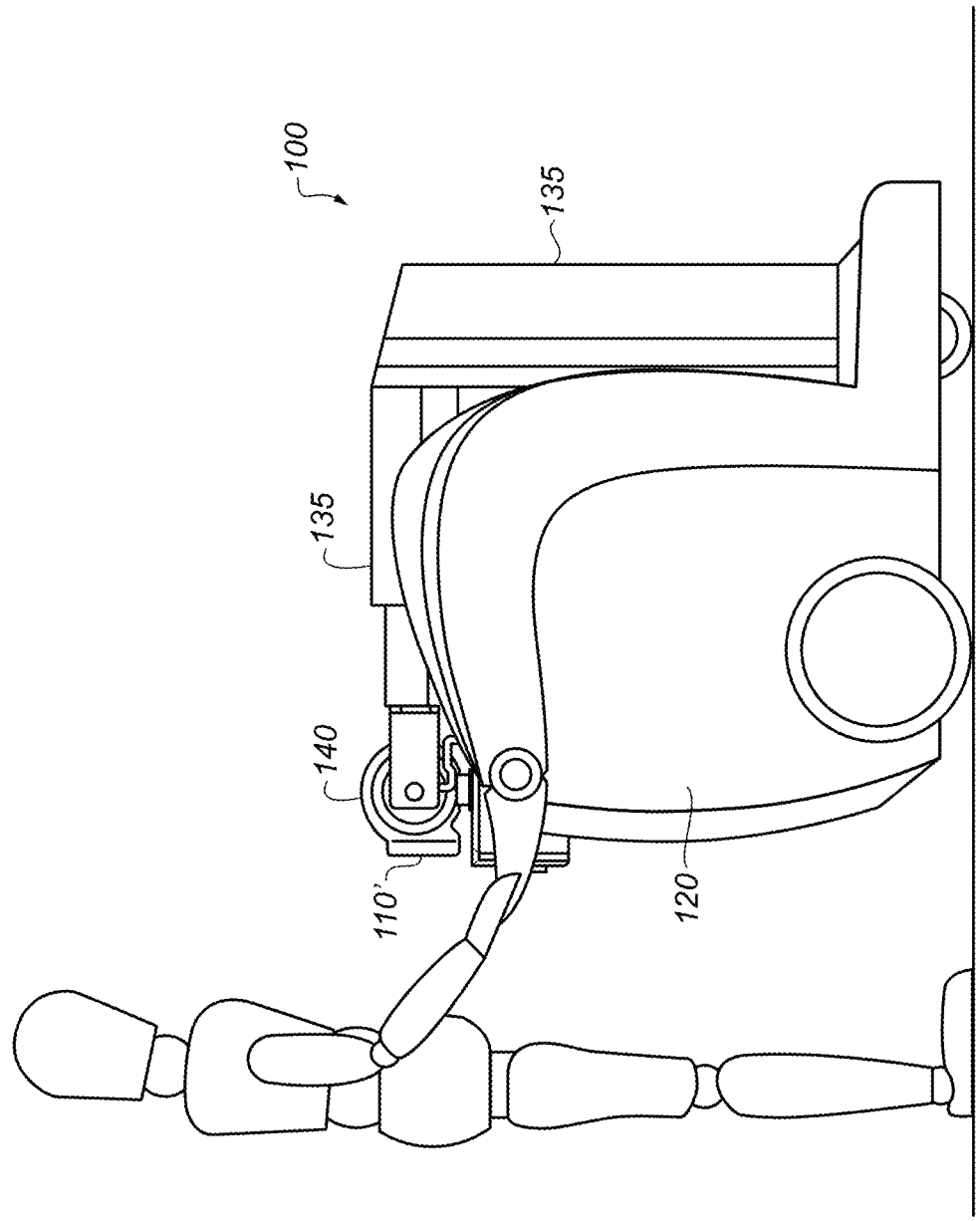
FIG. 2 is a diagram showing a perspective view of a mobile radiography unit of FIG. 1 positioned for travel.

As shown in FIG. 2, for ease during transport of the mobile radiographic apparatus 100, the support member 135 and x-ray source 140 can be arranged to seat closely to frame 120. As shown in FIG. 2, the second display 110' can be in a viewable position (e.g., operable) during transport of the mobile radiographic apparatus 100. When the mobile radiographic apparatus 100 is to be used, the support member 135 and x-ray source 140 can be extended from the frame 120 for proper positioning (e.g., by the operator, a user, or x-ray technician) and the second display 110' moved to viewable position such as shown in FIG. 1.

FIG. 3 is a diagram showing an exemplary embodiment of a display/monitor as a second display mounted to a boom assembly of a mobile radiography unit according to the application. As shown in FIG. 3, the second display 110' can be mounted to a collimator 345 of an x-ray source 340 of a support member 135 of a mobile radiography unit. In one embodiment, the collimator 345 can be rotatably mounted to the x-ray source 340 so that the collimator 345 (e.g., second display 110') can swivel at least 90 degrees, at least 180 degrees or 360 degrees. As shown in FIG. 3, the second display 110' is coupled to a plurality of handles for ease of positioning. Alternatively, the second display 110' can be mounted to (e.g., rotatably) x-ray source 340 above a collimator 345 of a boom assembly of a mobile radiography unit.

FIG. 4 is a diagram that illustrates an embodiment of a sign on screen according to the application. Thus, when an attempt is made to operate the mobile x-ray imaging apparatus 100, a sign on screen 410 can be displayed to provide instructions to a user. As shown in FIG. 4, the single sign on screen 410 can provide instructions for sign on sign on and activate the mobile x-ray system 100 such as "LOGIN: Please scan your badge or type User Name and Password at the main screen." Exemplary embodiments of a pass key or ID badge can include but are not intended to be limited to a card reader such as a smart card, a magnetic stripe card, bar code data, or a proximity reader compatible with access technologies such as RFID, bluetooth, wireless communication device, a proximity card, a wireless smart card, a wiegand card, a magnetic reader device/card, an optical reader device/card, an infrared reader device/card, or biometric data such as fingerprints, eye scan or the like.

According to embodiments of the application, the first display 110 and the second display 110' (FIG. 1) can provide capabilities/functionality to the mobile x-ray imaging apparatus 100 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm the correct patient); (iv) display and/or change a Patient Worklist, such as a list of exams to perform and allow the user to select an exam. (In one embodiment, such a patient worklist can be automatically updated (e.g., synchronized to a master/hospital/doctor worklist) using a wired or wireless network/connection. In one embodiment, the mobile x-ray imaging apparatus 100 can highlight/indicate new exams (e.g., on the second display 110') upon receipt of the scheduled examination.); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile x-ray imaging apparatus 100 during transport, e.g., using a video camera located on the other side (e.g., front side of the mobile x-ray imaging apparatus 100). In one embodiment, the mobile x-ray system 100 can include a collision avoidance system with alerts (e.g., audible, visual), and automatic maneuvering to avoid unnecessary contact in the examining room (e.g., by stopping or course modification).

Figure 7:
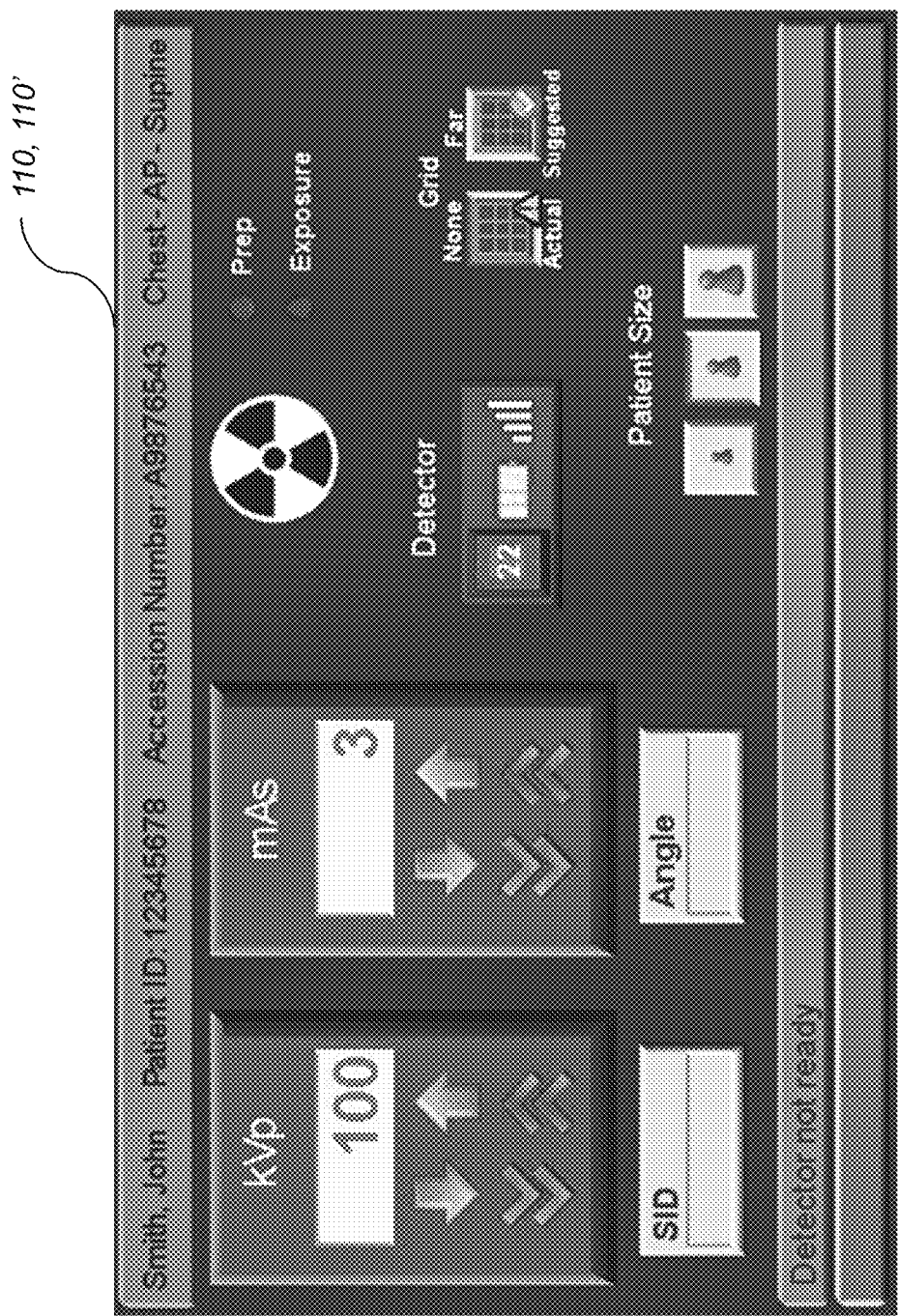
Figure 8:
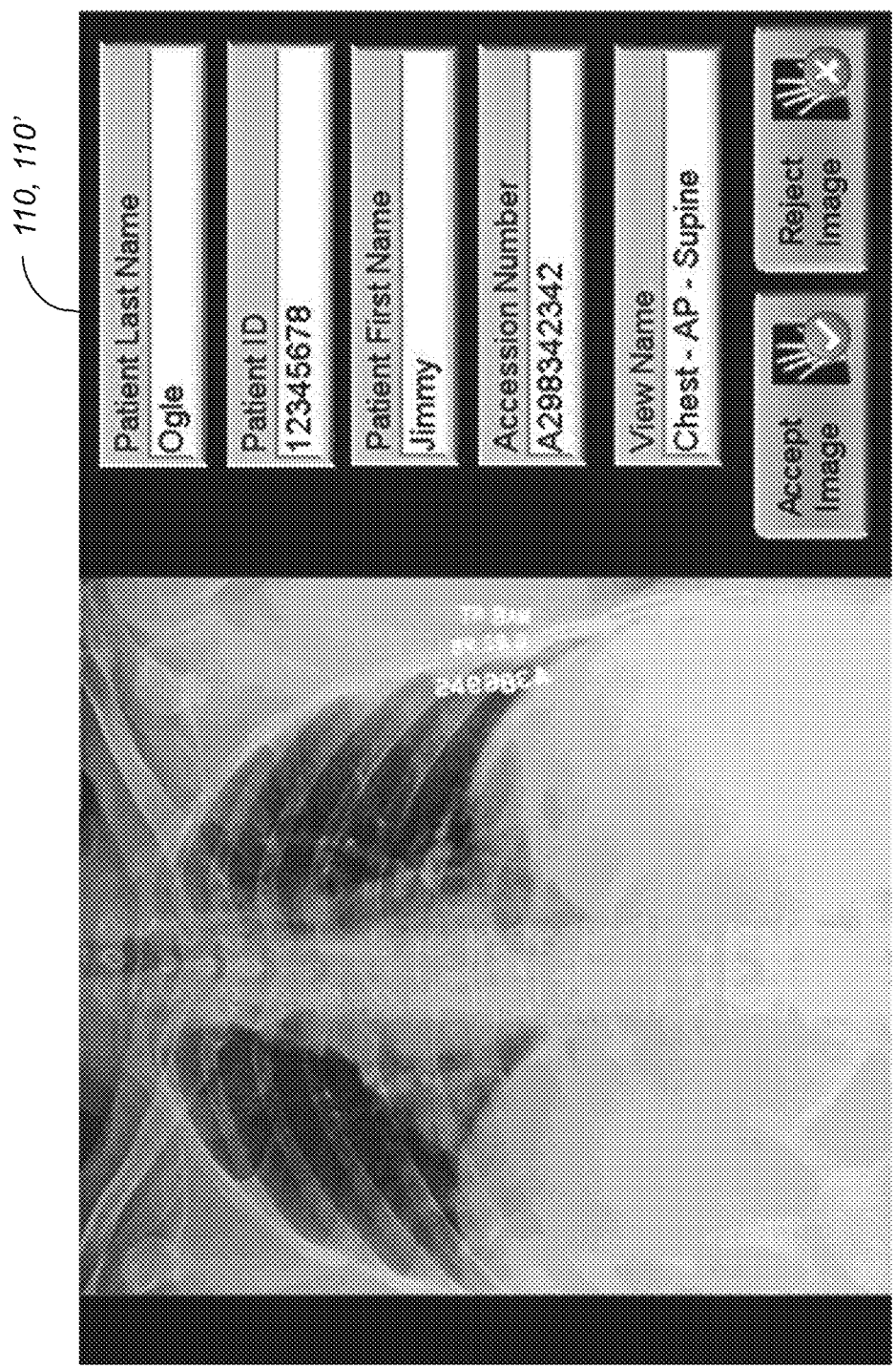

FIGS. 5-8 are diagrams that illustrate exemplary non-limiting representative functions illustrated on an embodiment of a second display of a mobile x-ray imaging apparatus as was shown in FIG. 1. As shown in FIG. 5, an example of a work list is shown on a monitor of the second display 110'. As shown in FIG. 6, an example of a new examination/procedure information/requirement for that technician and/or patient is shown on a monitor of the second display 110'. As shown in FIG. 7, an example of x-ray source controls is shown on a monitor of the second display 110'. As shown in FIG. 8, an example of newly acquired image and patient information is shown on a monitor of the second display 110'.

In one embodiment, the mobile radiographic imaging apparatus can be operated/controlled by programmed control logic in the first or second displays. For example, the programmed control logic can include a processor and display, an integrated computer system, or a portable computer and applications to operate thereon.

Figure 9:
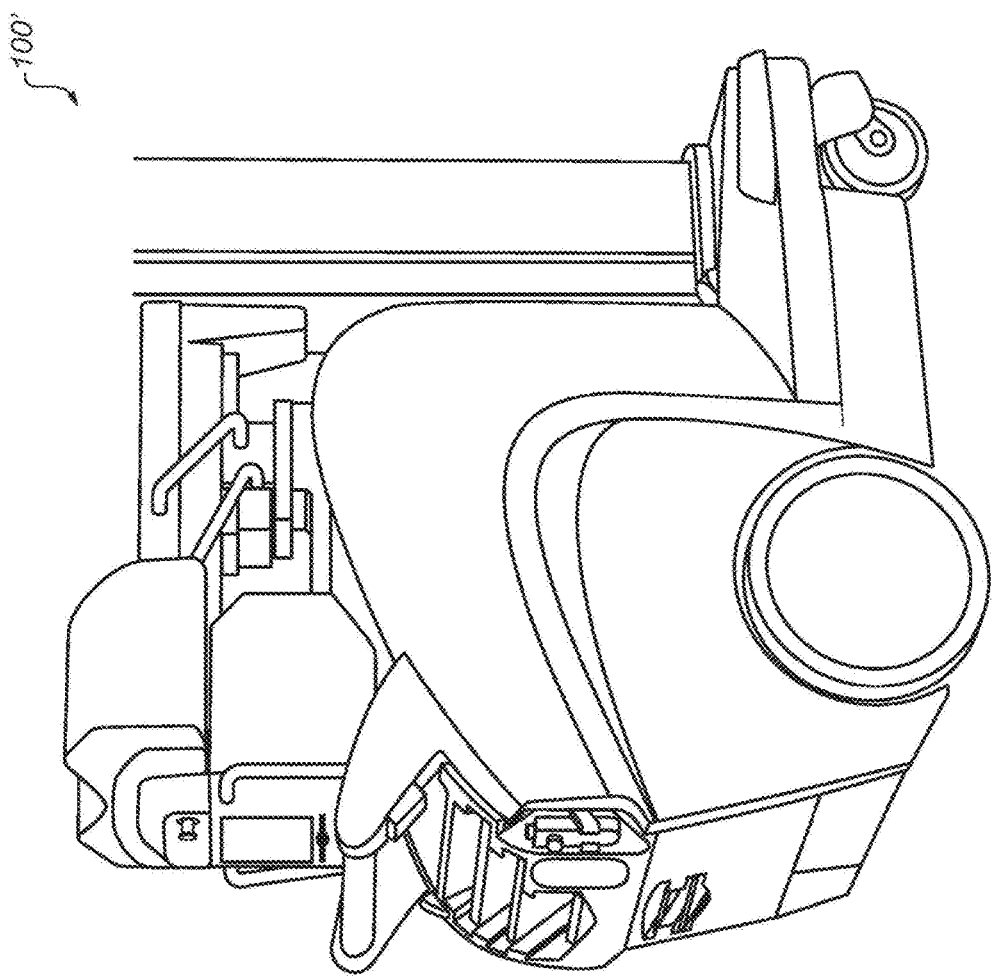
FIG. 9 is a diagram showing a perspective view of a mobile radiography unit according to another embodiment of the application.

FIG. 9 is a diagram showing a perspective view of a mobile radiography unit 100' according to another embodiment of the application.

Figure 10:
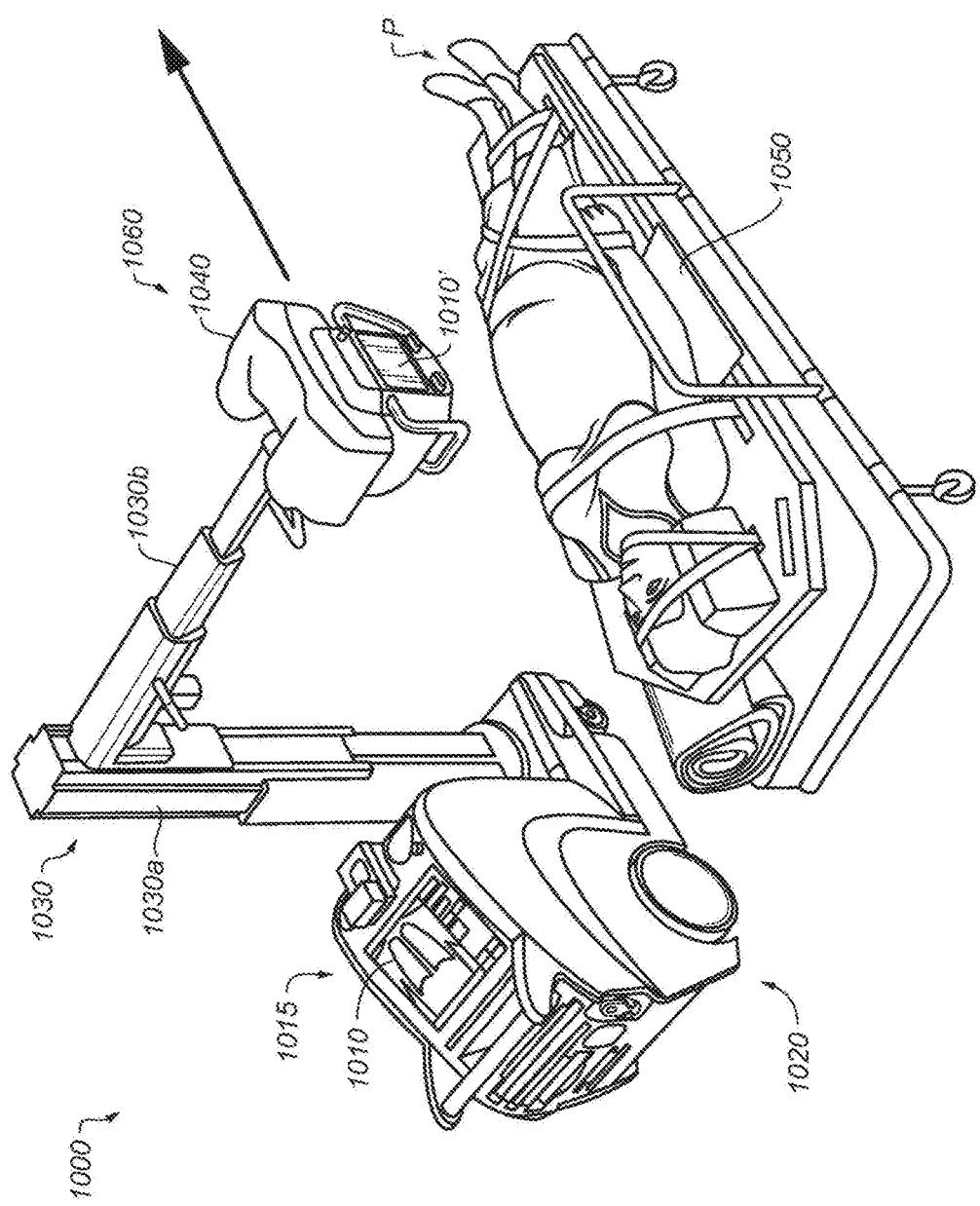
FIG. 10 is a diagram showing a perspective view of a mobile radiography unit that can provide a tomosynthesis capability according to embodiments of the present disclosure.

FIG. 10 is a diagram showing a perspective view of a mobile radiography unit that can provide a tomosynthesis capability according to embodiments of the application. In one embodiment, a mobile radiography unit can be a tomosynthesis system. As shown in FIG. 10, an embodiment of a portable tomosynthesis system 1000 is shown that can include a movable transport frame 1020. Mounted to the moveable transport frame 1020 can be a support column that supports an x-ray source 1040 as part of an x-ray source assembly 1060. As shown in FIG. 10, a support column 1030 can include a second section 1030b that extends outward a fixed/variable distance from a first section 1030a where the second section 1030b is configured to ride vertically up and down the first section 1030a to the desired height for obtaining the projection images. The system also includes a digital x-ray detector 1050 that is wirelessly or by wire connected to a system controller 1015 contained inside the moveable transport frame 1020. The system controller 1015 can implement and/or control the functionality of the mobile radiographic unit 1000 (e.g., functionality provided through the displays 100, 100'). The system controller 1015 can be provided though one or more of a conventional general purpose processor, digital computer, microprocessor. RISC processor, signal processor. CPU, arithmetic logic unit (ALU), video digital signal processor (VDSP) and/or similar computational machines, programmed according to the teachings of the application, as will be apparent to those skilled in the relevant art(s).

The x-ray source 1040 can use a collimator to form beams that are directed towards the detector 1050. The x-ray source 1040 may also include positioning, such as motors, which allow for directing the beam towards the detector. The moveable transport frame 1020 can include a first display 1010 and the x-ray source 1040 can be coupled to a second optional display 1010'. The system controller 1015 can coordinate operations of the x-ray source 1040, detector 1050, and moveable transport frame 1020. The system controller 1015 can control operations of the x-ray source, which may include the collimator, positioning devices and triggering of image acquisition by emission of x-rays from the source. The system controller 1015 also can control operations of the detector 1050, which may include triggering of the image acquisition and transmission of the acquired images back to the controller. In addition, the system controller 1015 can control the movement of the transport frame 1020.

FIG. 10 shows an embodiment of a portable tomosynthesis system where the x-ray source 1040 assembly can be moved along a prescribed path relative to the detector 1050 or relative to geometry of the detector 1050 and/or a patient (object) to be imaged. As shown in FIG. 10, the moveable transport frame 1020 can move the x-ray source 1040 assembly along a prescribed path (e.g., linear/non-linear motion) illustrated by an arrow.

Figure 11A:
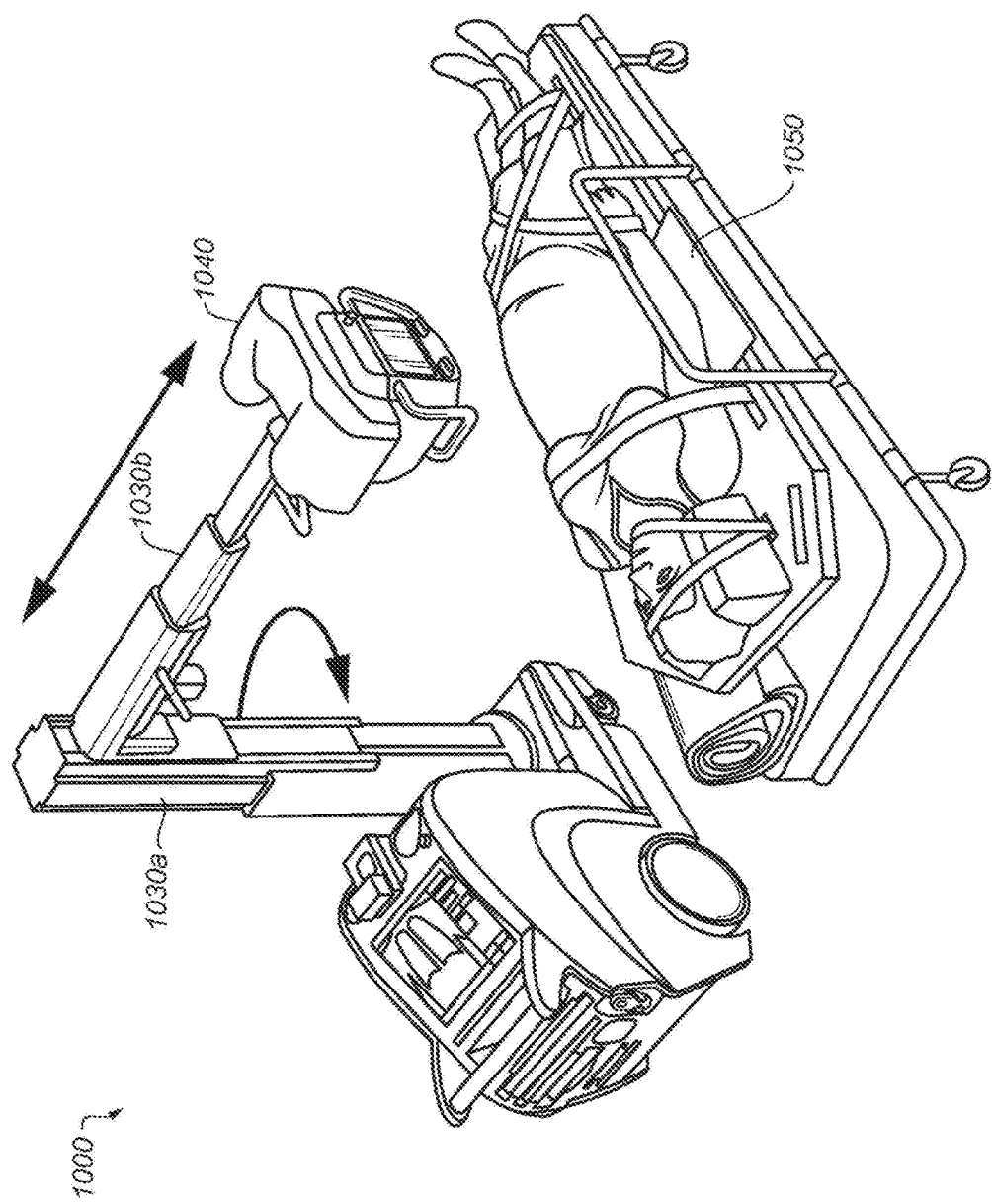
FIGS. 11A-11B are diagrams that show perspective views of alternative mobile radiography units that can provide a tomosynthesis capability according to embodiments of the present disclosure.
Figure 11B:
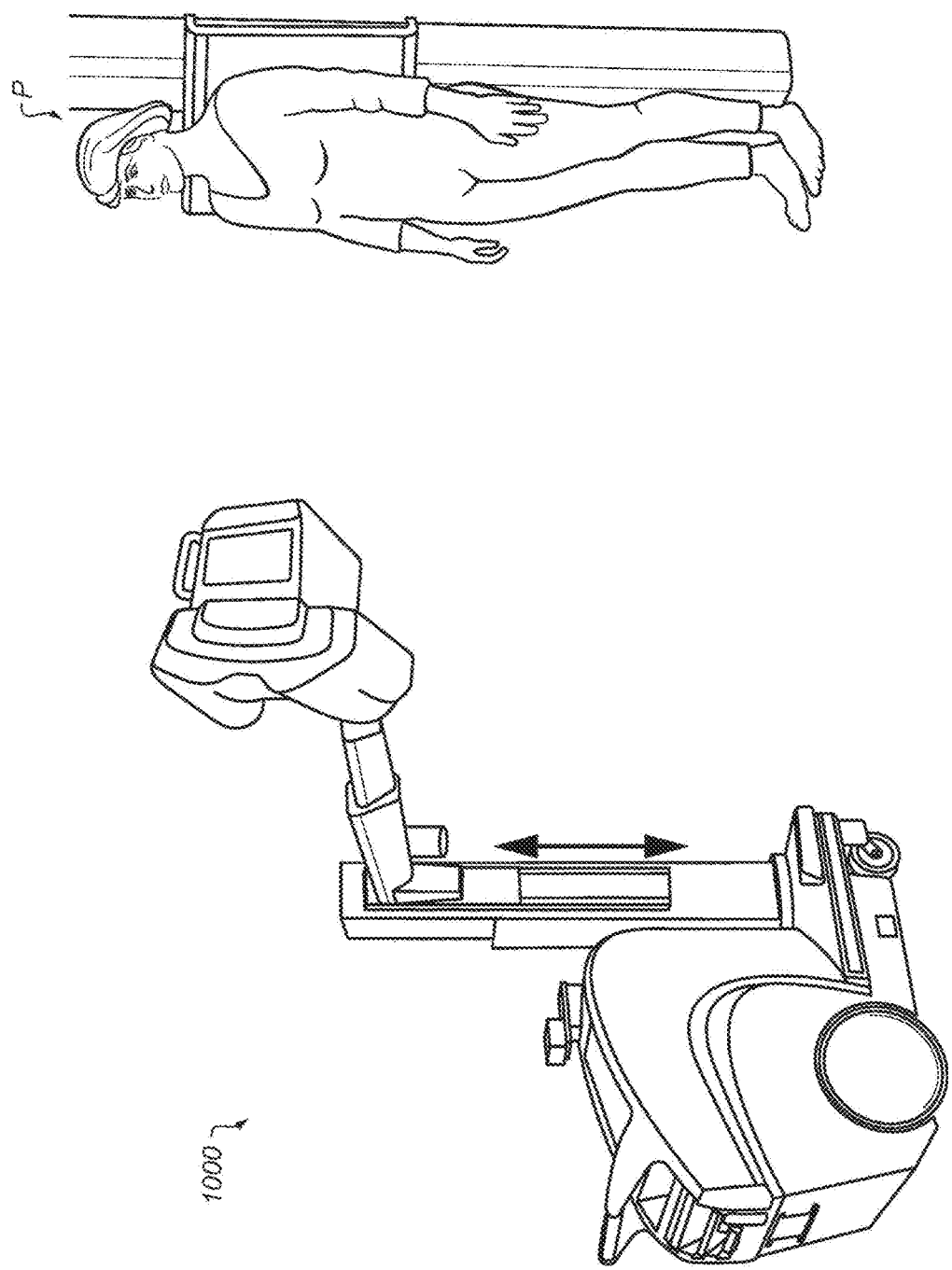

FIGS. 11A-11B are diagrams that show perspective views of additional mobile radiography units that can provide tomosynthesis capabilities according to embodiments of the application. As shown in FIG. 11A, the support column 1030 can move the x-ray source 1040 assembly along a prescribed path (e.g., linear/non-linear, curved, 2D or 3D) illustrated by an arrows. In certain exemplary embodiments, the second section 1030b and/or the first section 1030a can independently move the x-ray source 1040 assembly or move the x-ray source 1040 assembly in combination (e.g., concurrently). Further, the moveable transport frame 1020 can move the x-ray source 1040 assembly in combination with the support column 1030. In one embodiment, the mobile radiography units can include a tomosynthesis capability for a patient P as shown in FIG. 11B can further be used for LLI (Long Length Imaging).

Figure 12:
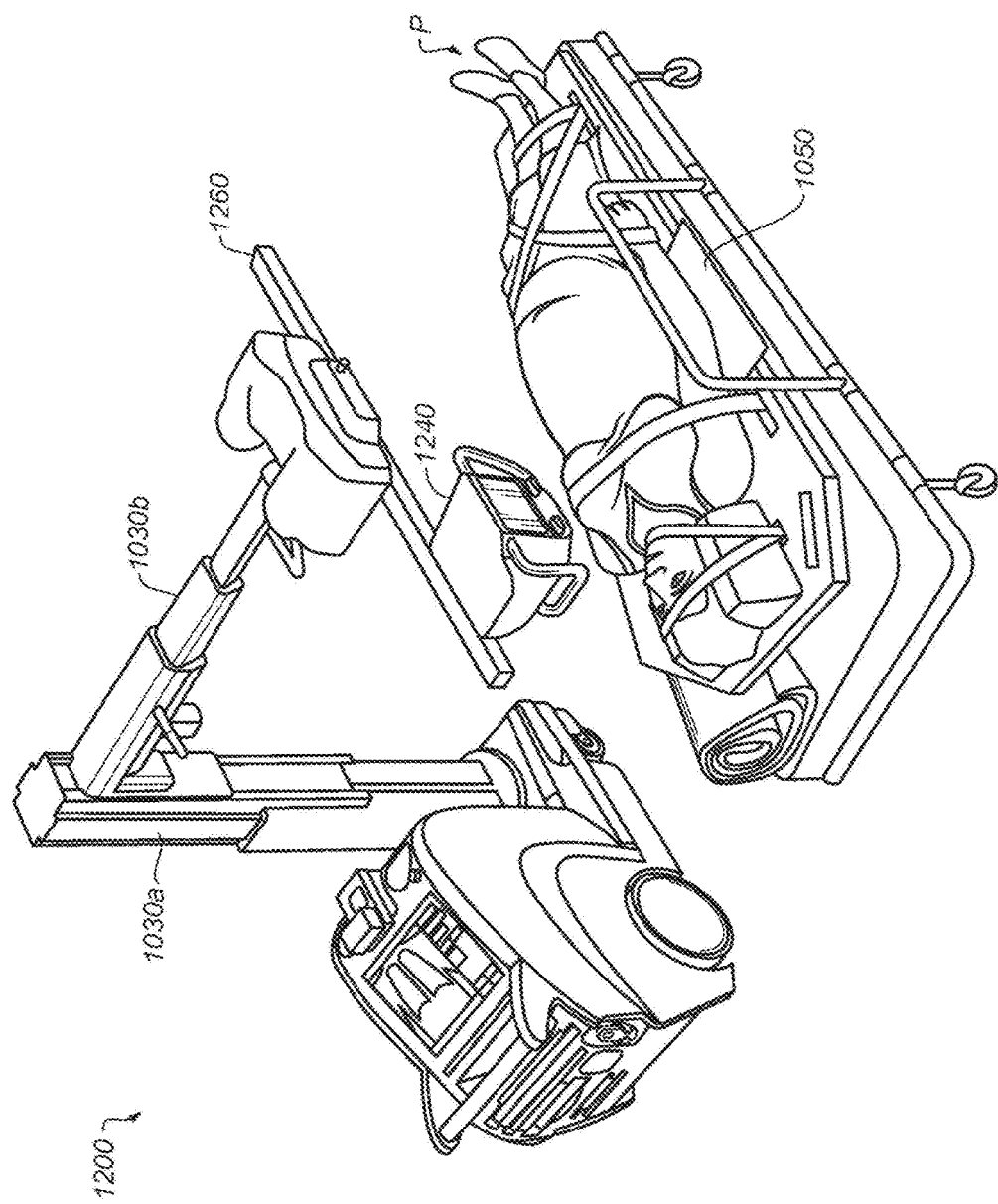
FIG. 12 is a diagram showing a perspective view of another mobile radiography unit that can provide a tomosynthesis capability according to embodiments of the present disclosure.

FIG. 12 is a diagram showing a perspective view of another mobile radiography unit 1200 that can provide a tomosynthesis capability according to embodiments of the application. In one embodiment of a portable tomosynthesis system, an x-ray source assembly can be configured to move along a prescribed path (e.g., linear path). FIG. 12 shows an embodiment of a portable tomosynthesis system where the x-ray source assembly is replaced by an X-ray source 1240 designed to move along a linear path on a support track 1260.

Figure 13:
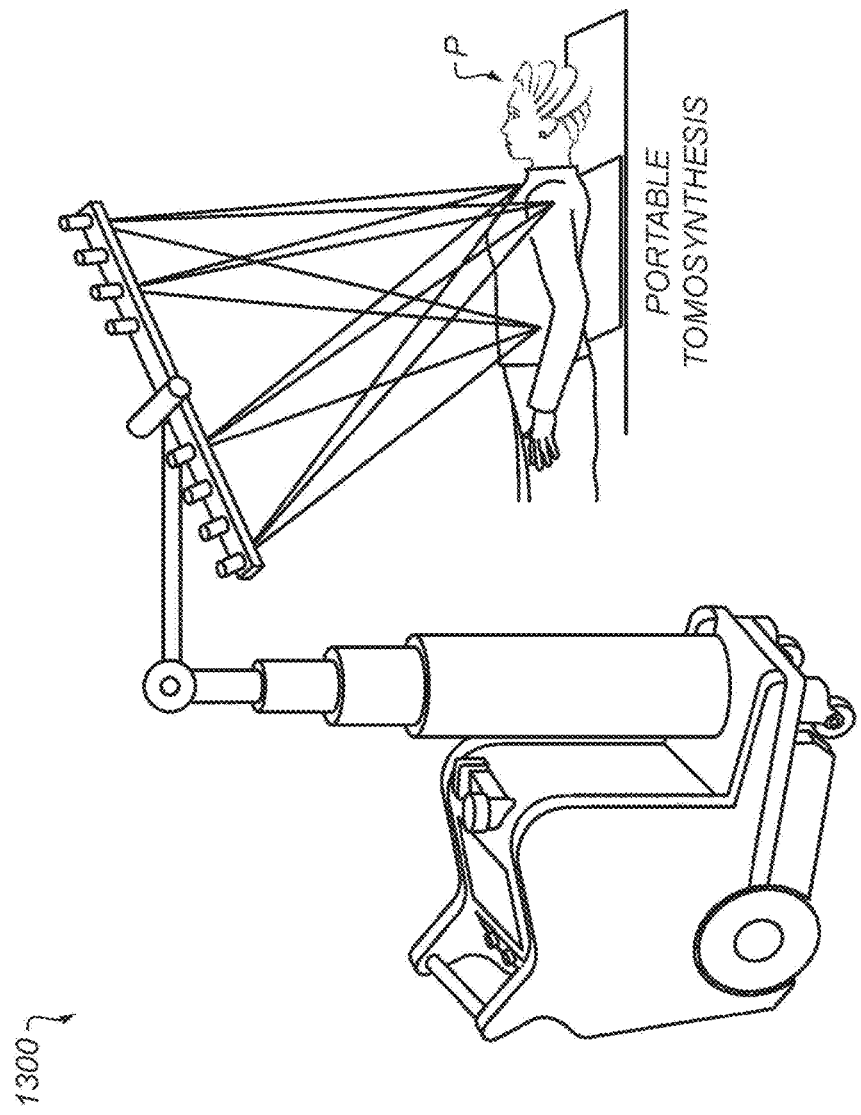
FIG. 13 is a diagram showing a perspective view of yet another mobile radiography unit that can provide a tomosynthesis capability according to embodiments of the present disclosure.

FIG. 13 is a diagram showing a perspective view of another mobile radiography unit 1300 that can provide a tomosynthesis capability according to embodiments of the application. In certain exemplary embodiments of portable tomosynthesis systems, the moveable mounted x-ray source can be replaced by a plurality of multiple individually controlled x-rays sources. FIG. 13 shows an embodiment of a portable tomosynthesis system where the multiple individually controlled x-rays sources are distributed sources (e.g., linearly distributed). The distributed sources can be arrayed in a prescribed spatial relationship.

Alternatively, different x-ray source paths can be used to modify or address reconstruction artifacts that can be caused by limited angular scanning systems such as radiographic tomosynthesis imaging systems. In addition, various x-ray scan paths can be used to accentuate the desired imaged structures and/or reduce or minimize artifacts that might confound or mask the ability to make an accurate diagnosis.

Figure 14:
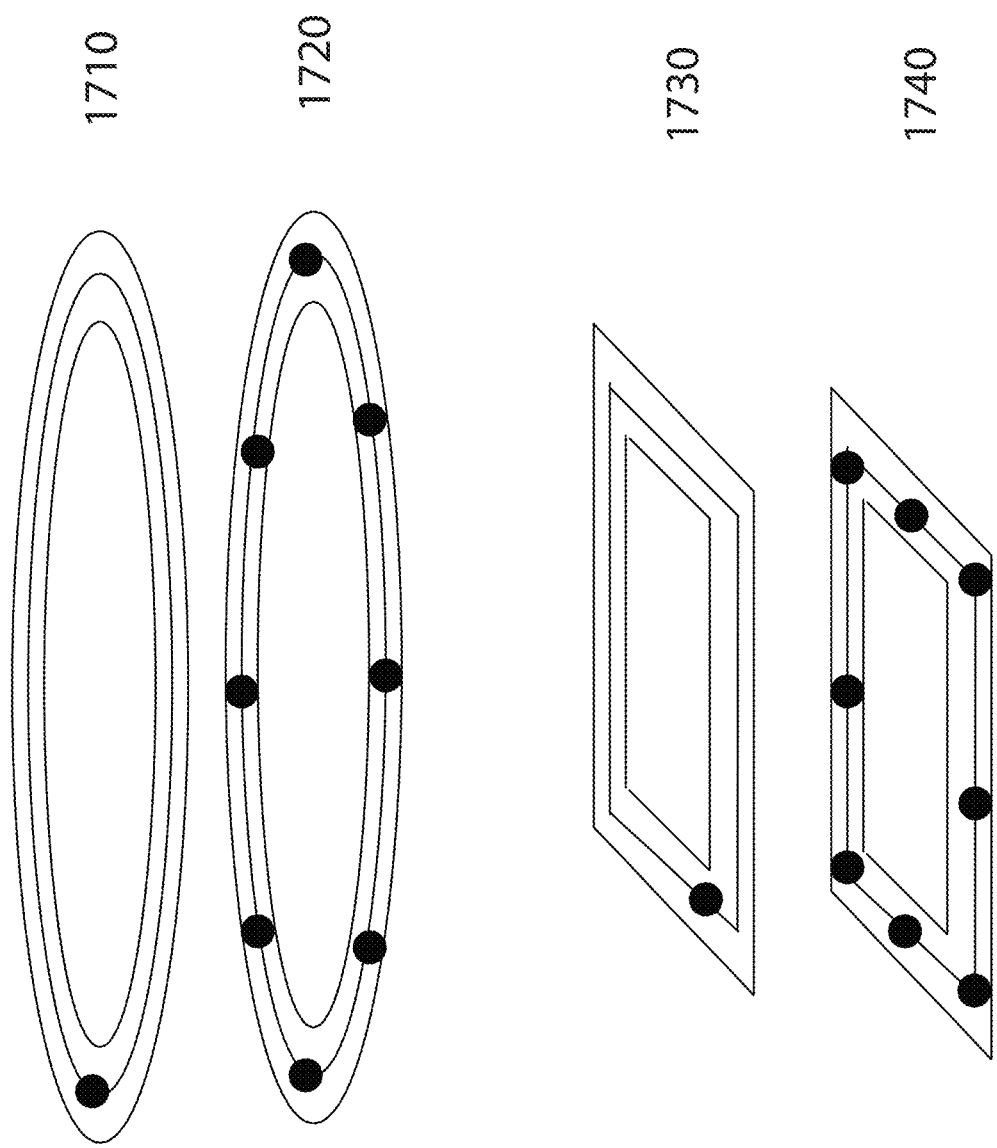
FIG. 14 is a diagram showing examples of non-linear x-ray scan paths according to embodiments of the present disclosure.

FIG. 14 is a diagram showing examples of non-linear x-ray scan paths (e.g., circular and square paths). In one embodiment, the moveable x-ray source is mounted on a circular 1710 (square 1730) track or a plurality of sources are spatially distributed in a circular 1720 (square 1740) pattern. However, embodiments of the application are not intended to be so limited, for example other non-linear, curved, 2D or 3D scan paths or movable x-ray supports can be used. Further, source assemblies can be used to ensure that radiation emitted by the moveable or distributed x-ray source is directed towards the detector (e.g., through the object/patient). In one embodiment, the source assemblies can include adjustable collimators (e.g., before or during an image acquisition scan). In one embodiment, the adjustable collimators can be individually and/or concurrently moved.

In one embodiment, a mobile radiographic imaging system is intended to support critically ill patients in an ICU that are currently transported out of ICU for x-ray imaging. For example, ICU patients can receive a tomosynthesis procedure; otherwise, these patients might need to be transported out of ICU in order to obtain a CT exam. For example, CT imaging is often needed for ICU patients in order to differentiate various types of fluids induced by plural effusions, such as blood, water, and the like, so that corrective actions can be taken. However, transporting ICU patients to the CT exam area can be a challenging task due to their severe clinical conditions. Further, visualization software can be provided to facilitate interpretation of ICU-related chest abnormalities. For instance, presentation of the low exposure sequences (prior to reconstruction of the slide data) may allow the ICU physician to "look around" rib structures and the like.

As is shown schematically in the arrangements of FIGS. 10-13, the x-ray detector is positionally uncoupled from the x-ray source. Alternately stated, the detector and source are mechanically uncoupled; there is no mechanically fixed spatial arrangement for source-detector positioning. The operator attempts to approximate an appropriate angular and distance relationship between the source and detector; however, this relationship is at best, a close approximation of a recommended distance for the patient anatomy being imaged.

Figure 15:
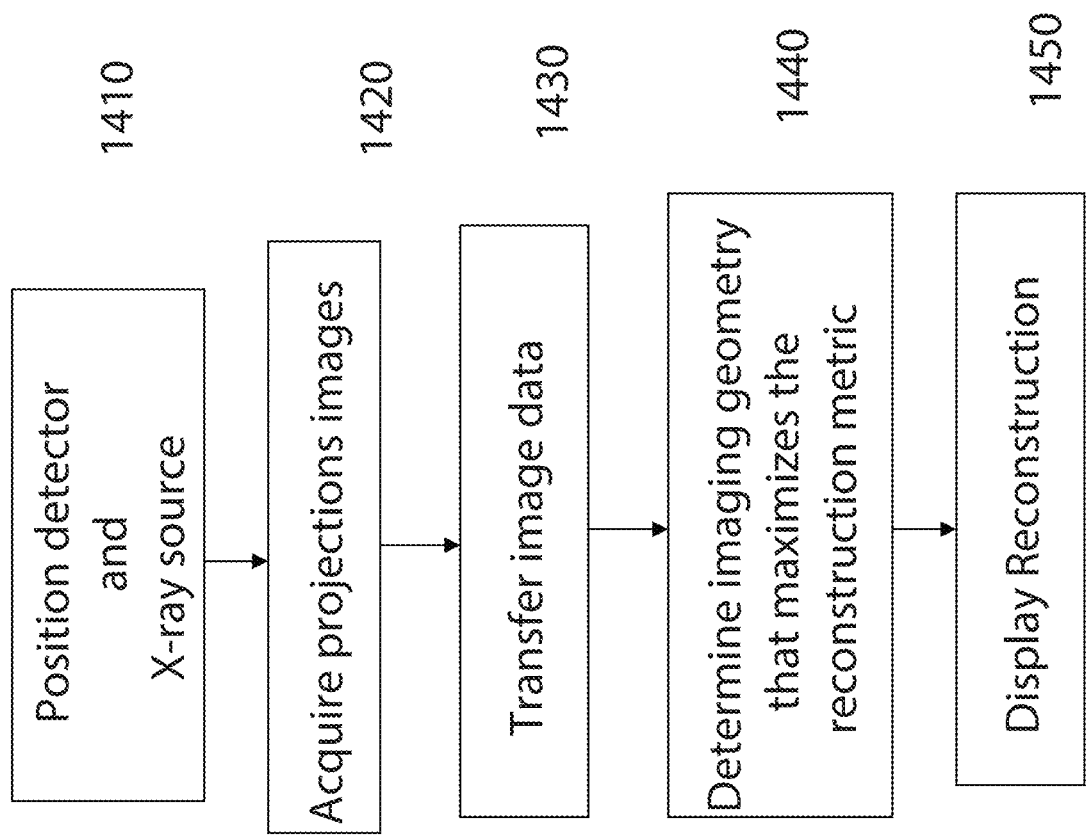
FIG. 15 is a flow chart showing an exemplary method of operating exemplary mobile radiographic imaging systems for acquiring projection images and generating reconstructions of (e.g., three-dimensional) tomosynthesis images according to embodiments of the present disclosure.

Referring to FIG. 15, a flow chart shows an exemplary method of acquiring projections images and generating the reconstruction of three-dimensional tomosynthesis images. The method for acquiring projection images and generating the reconstruction of three-dimensional tomosynthesis images will be described using embodiments of mobile radiography apparatus shown in FIGS. 10-13 and can be applied to mobile x-ray systems/carts shown in FIGS. 1 and 10-13; however, the method of FIG. 15 is not intended to be limited thereby.

As shown in FIG. 15, the detector and x-ray source can be positioned (operation block 1410). For example, the x-ray source can be moved to its initial position and the detector can be positioned such that the patient P is interposed between the detector and x-ray source.

For exemplary portable tomosynthesis system embodiments 1000, 1200, 1300, the initial x-ray source assembly position can be set by the location of the transport frame and the support column. The height, extent and rotation positioning of the support column's first section 1030a and the second section 1030b can be used to position the x-ray source assembly to the initial desired location above the patient the patient. Alternatively, the support (e.g., support 1260, track 1710, track 1730) and the location of the transport frame and/or the support column can set the initial x-ray source assembly position.

A series of projections image can be acquired at different x-ray source positions (operation block 1420). In embodiment 1000, the projection images can be acquired while the transport frame, and thus attached x-ray source, is moved along a linear or non-linear path. In embodiment 1000, the projection images can be acquired while the height, extent, and rotation of the support columns first and second section are modulated so that the attached x-ray source, is moved along a linear or non-linear path. In embodiment 1200 of FIG. 12, the projection images can be acquired while the x-ray source is moved along the support track. In embodiment 1300 of FIG. 13, the projection images can be acquired while individual x-ray sources are triggered.

Then, following the sequence of FIG. 15, the acquired projection image data can be received (e.g., transfer back from the detector to) by control and processing components of the system controller (operation block 1430). The projection images can be displayed on display 110 and/or undergo a quality check (e.g., automated or by the operator) before being further processed. The imaging geometry that corresponds to a predetermined reconstruction metric, such as an image quality metric related to gradient, histogram, or entropy of the reconstructed object, is determined in an operation block 1440.

Then, the reconstruction volume can be displayed on display 110, 110' (operation block 1450) and/or undergo a quality check before storing the volume. In one embodiment, the reconstruction volume can be stored after the quality check (e.g., before display thereof).

An example of a data fidelity metric is:

$$E_5 = \frac{1}{2} \sum_{i=1}^{nProjs} \|A_i f - p_i\|^2$$

or a regularized version, $$E_6 = R(f) + \frac{1}{2} \sum_{i=1}^{nProjs} \|A_i f - p_i\|^2$$

wherein $A_i$ is the projection matrix for the ith projection, f and p are vector representations of the reconstruction volume and projection images, and R( ) is a regularizer imposing a prior, such as smoothness, on the reconstruction f. The projection matrices A are a function of the imaging geometry.

The image quality of the reconstruction depends, in part, upon the accurate knowledge of the position of the x-ray source and detector for each projection. Uncertainties in the scan geometry can lead to artifacts and/or blurring in the reconstruction. Further, accurate positioning of the detector using a grid can be desirable or fundamental to allow impinging x-rays to pass the grid to reach, in whole or in part, the detector. For a portable stationary detector tomosynthesis system, the scan geometry can correspond to the set x-ray source locations relative to the stationary detector. The position encoders associated with the moveable frame and moveable x-ray source assembly can provide accurate information about the spatial location of the x-ray source in a local coordinate system associated with the x-ray source assembly. For a distributed source assembly, the spatial location of x-ray sources can be fixed in the local coordinate system. For the portable tomosynthesis system, the detector and x-ray source are physically separated from each other. As a consequence, the relative orientation and distance between the x-ray source assembly and the detector local coordinate systems are not fixed or accurately known beforehand. In one exemplary embodiment, a detector can be physically separated and tethered to the portable tomosynthesis system, however, such system geometry (e.g., position, orientation etc. of detector, x-ray source(s)) can be unknown.

Figure 16:
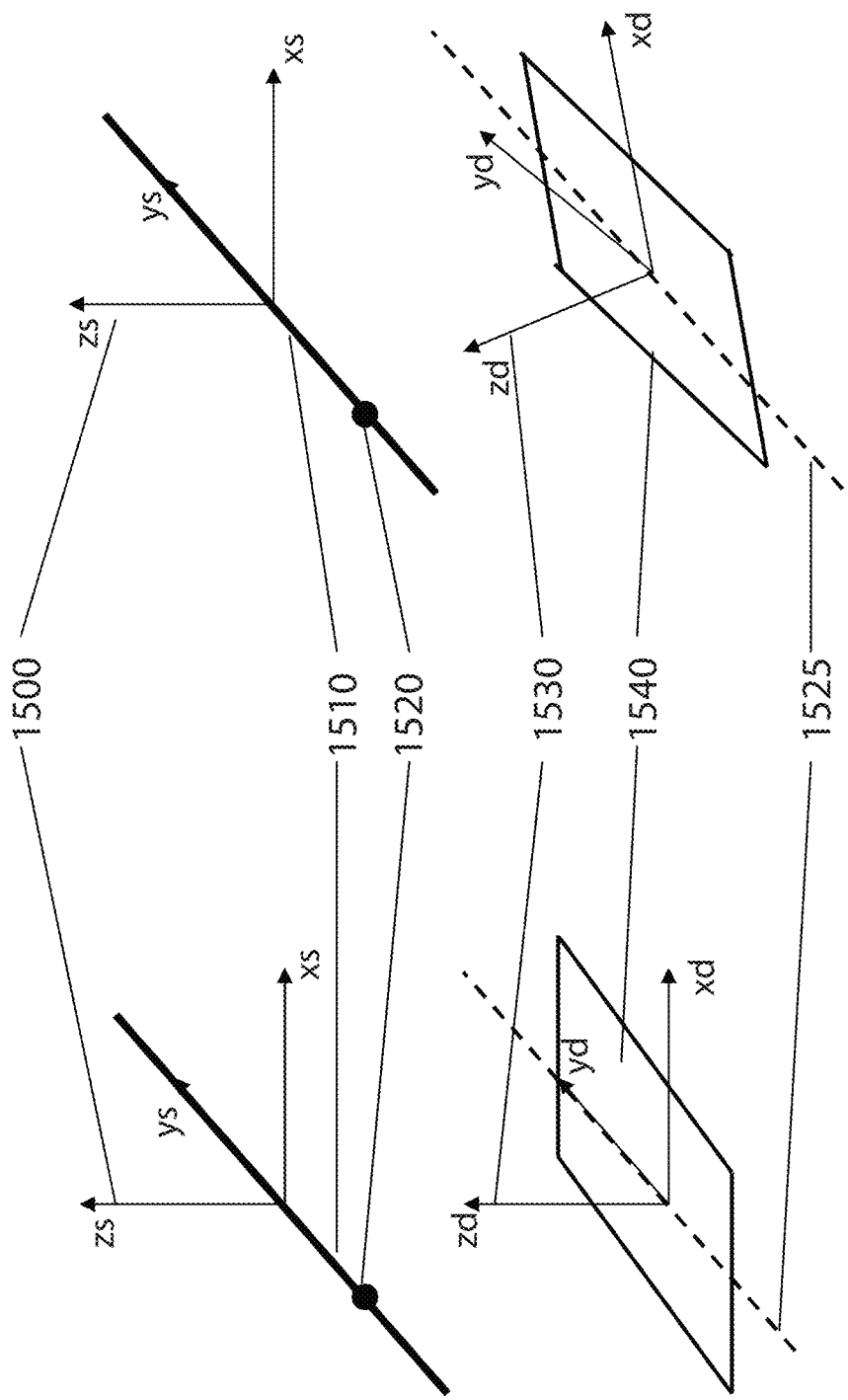
FIG. 16 shows diagrams that schematically show exemplary relative orientation and distance between an x-ray source coordinate system and an detector coordinate system for a linear scan tomosynthesis system according to embodiments of the present disclosure.

FIG. 16 is a schematic diagram showing exemplary relative orientation and distance between x-ray source coordinate system 1500 with coordinates ($x_s$, $y_s$, $z_s$) and the detector coordinate system 1530 with coordinates ($x_d$, $y_d$, $z_d$) for a linear scan tomosynthesis system.

The left side of FIG. 16 shows a desired aligned tomosynthesis system (e.g., selected alignment or ideally aligned), where the detector and x-ray source coordinates have the same orientation. A projection 1525 of the trajectory 1510 of the x-ray source 1520 onto the detector 1540 is aligned with the one of the detector's in-plane axes and the distance between the x-ray source and detector along the x-ray source's trajectory is constant.

The right side of FIG. 16 shows a system where the detector and x-ray source coordinates have different orientations so that, as a result, the distance of the x-ray source to the detector plane now varies along the x-ray source trajectory. As was shown in FIG. 12, this type of mismatch in orientation between the x-ray source assembly 1060 and detector 1050 can occur when the detector 1050 is placed under a bedridden patient.

The imaging parameters can be the set or some subset of x-ray source locations $\{xs_i, ys_i, zs_i\}$ relative to the stationary detector for each projection image used in the reconstruction. Alternatively, if the distances between the x-ray source locations are known, as described above, then the imaging parameters correspond to the relative orientation and distance between the x-ray source assembly and the detector. This corresponds to determining the set or subset of rigid motion parameters that convert the assumed nominal x-ray source positions to positions in space that optimize the reconstruction metric.

Figure 17:
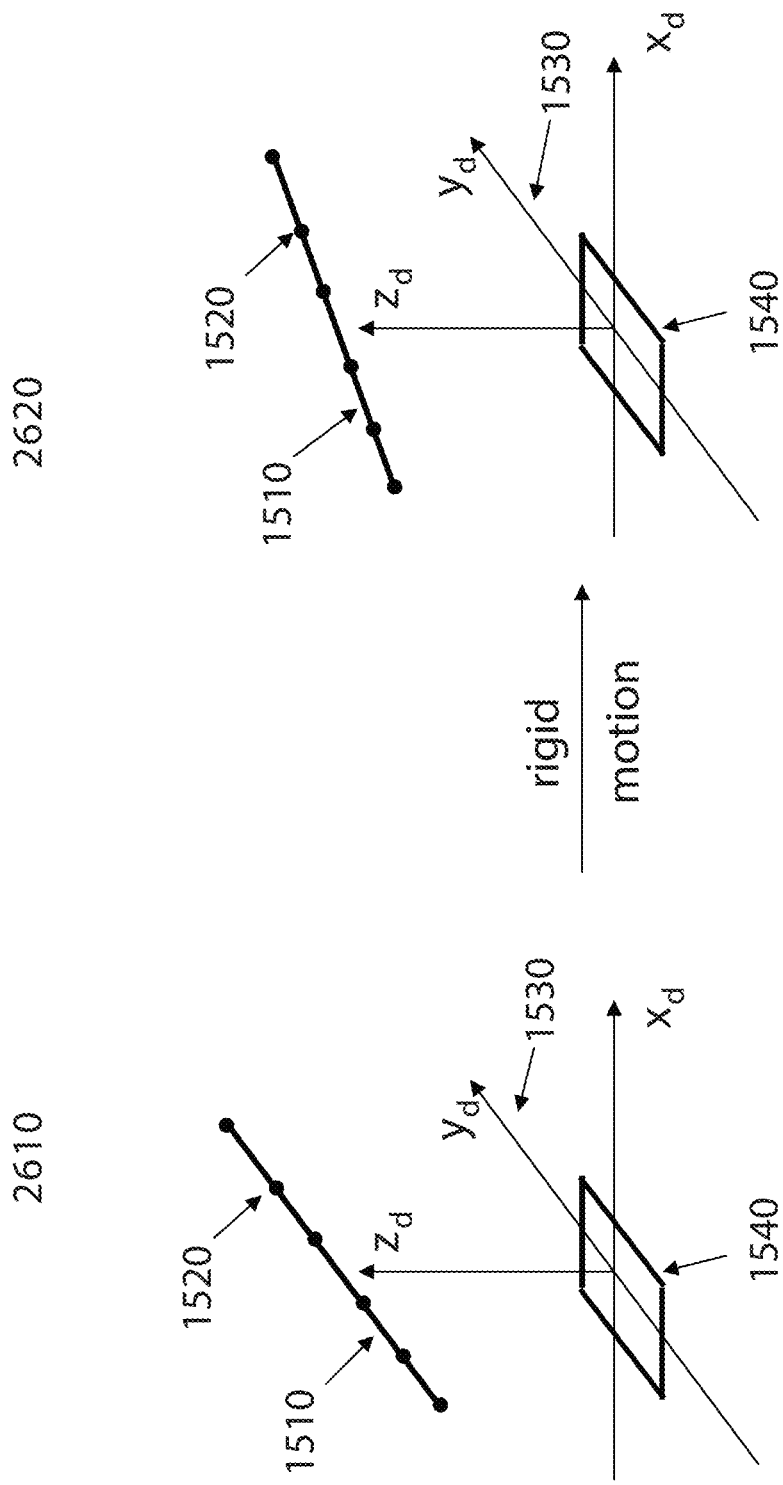
FIG. 17 is a diagram that schematically shows an exemplary resulting orientation and distance of a linear track x-ray source assembly after applying rigid motion to a starting orientation and distance of a linear track x-ray source assembly according to embodiments of the present disclosure.

FIG. 17 is a diagram showing an exemplary resulting orientation and distance of a linear track x-ray source assembly 2620 after applying rigid motion to the starting orientation and distance of a linear track x-ray source assembly 2610. The set rigid motion parameters can be the rotations θx, θy, θz along the detector's $x_d$, $y_d$, and $z_d$ axes.

Figure 18:
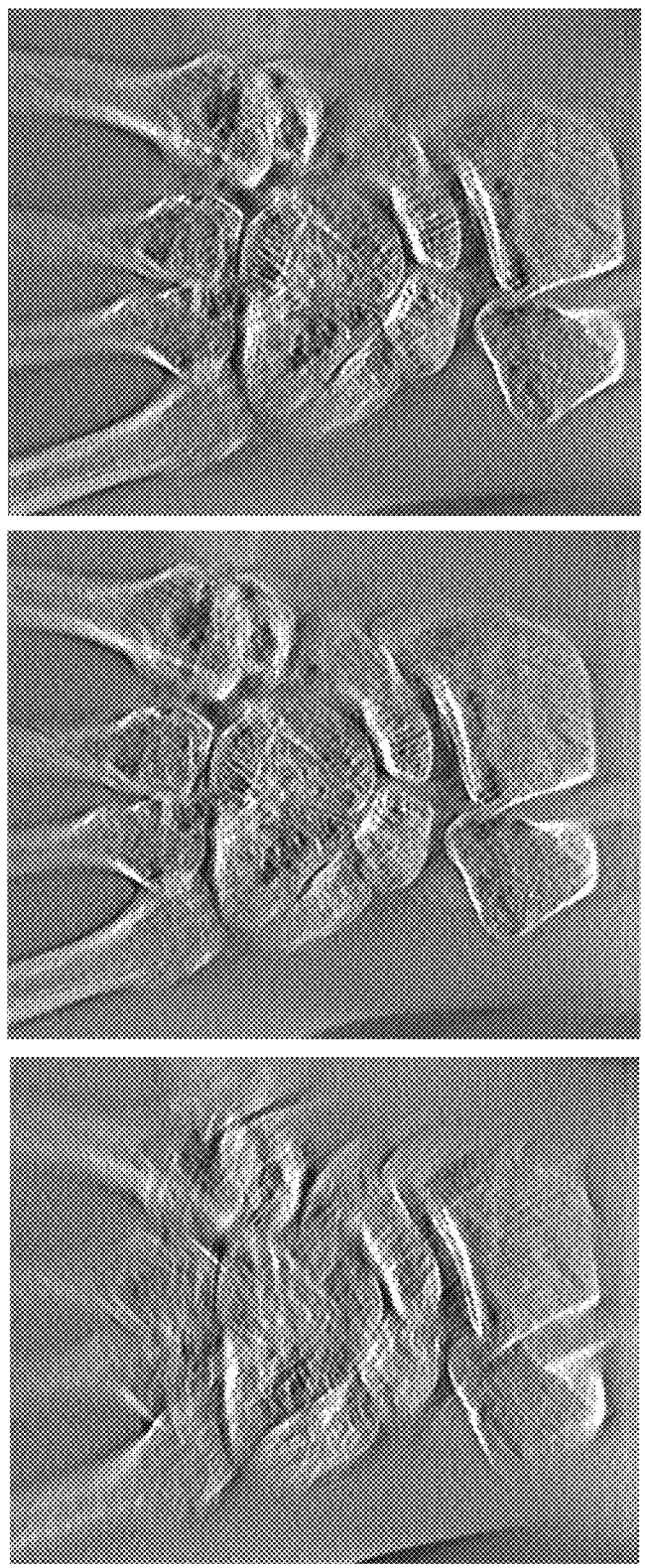
FIG. 18 is a diagram showing a slice of the tomosynthesis reconstruction for an exemplary linear track scan using an assumed imaging geometry, a modified geometry as determined using imaging geometry auto-correction reconstruction, and an actual imaging geometry according to embodiments of the present disclosure.

FIG. 18 is a diagram showing a slice of the tomosynthesis reconstruction for a linear track scan of a hand phantom using the assumed imaging geometry 1810, the optimized geometry 1820 as determined by an imaging geometry auto-correction reconstruction algorithm, and the actual imaging geometry 1830. For the assumed geometry the x-ray source assembly is translated 180 cm along the detector's z axis and has the same orientation as the detector. The actual geometry corresponds to the linear track being rotated −3.9 degree about its x axis followed by a −3.9 degree rotation about its z axis from its assumed position. As shown in FIG. 18, tomosynthesis reconstruction results using the imaging geometry calculated from the auto-correction reconstruction algorithm and the actual imaging geometry are essentially indistinguishable.

Various exemplary embodiments described herein can illustrate individual modes of operation. In certain exemplary embodiments, more than one mode can be provided in/by a single mobile radiographic imaging system and/or methods for using the same.

Certain exemplary embodiments of mobile radiographic imaging systems and/or methods for using the same can determine or use auto-correction reconstruction processes that can produce data in a unified coordinate system, for each image in a capture sequence that provides the relative x-ray source focal spot position and detector position and orientation. This information can have various multiple uses in tomosynthesis image reconstruction. For example, such information can be used in conjunction with X-ray exposure technique technical factors to estimate the signal the detector would receive with an "air exposure" (e.g., without any object/subject interposed between the source(s) and the detector). This "air exposure" image can be used in tomosynthesis reconstruction to provide the estimated linear attenuation coefficients for volumetric reconstruction processing. Further, a recovered geometry according to the application can also be used to apply tomosynthesis reconstruction approaches employing other methods such as SIRT (Simultaneous Iterative Reconstruction Technique). SART (Simultaneous Algebraic Reconstruction Technique), ART (Algebraic Reconstruction Technique) or other methods known by those skilled in the art of volumetric reconstruction algorithms. In addition, recovered geometry can also be used in patient dose estimation.

FIG. 19 is a diagram showing a mobile radiographic imaging system that can include first and second (e.g., multiple) radiographic x-ray sources. As shown in FIG. 19, a mobile radiographic imaging system can include a first radiographic x-ray source and collimator, and a second x-ray source comprising a distributed source (e.g., rectangle) that can be either permanently attached or attached (detachable) when needed.

FIG. 20 is a diagram showing a mobile radiographic imaging system that can include first and second (e.g., multiple) radiographic x-ray sources. As shown in FIG. 20, a mobile radiographic imaging system can include a first radiographic x-ray source and collimator, and a second x-ray source comprising a distributed source attachment (e.g., linear) that can be either permanently attached or attached (detachable) when needed. In one embodiment, the distributed sources can be on a curved support to maintain a single distance from a corresponding point on a detector. Exemplary distributed source attachment can have a first position for use and a second position for storage (e.g., folded) when not used. In one embodiment, exemplary distributed source attachments can have a first position for use, at least one intermediate position (e.g., half-unfolded) and a second position for storage (e.g., folded) when not used. In one embodiment, such exemplary distributed sources can be replaced by a track and a moving x-ray source.

Calibration Using Epipolar Geometry

Embodiments of the present disclosure address the problem of geometric calibration for portable tomosynthesis, using imaging components of a mobile radiography apparatus. Unlike methods available with conventional tomosynthesis systems, the mobile radiography apparatus does not have fixed source-detector geometry. Instead, since source-detector positioning varies with each exam, calibration information must be extracted from the data obtained in successive projection images.

Tomosynthesis reconstruction requires capture of a succession of images of the subject over a range of angles, with the x-ray source and detector geometry well known at each of the image capture positions. The system can work with either or both the source and detector changing positions. With mobile radiography apparatus, the position of the x-ray detector typically remains fixed behind the patient, for reasons described previously. The x-ray source is translated over a linear or curved travel path, allowing image acquisition at each of a predetermined set of acquisition angles. A reconstruction algorithm uses the geometry of the captured 2D projection images to transform the collection of 2D projection images into a volumetric data set. However, with mobile radiography apparatus, the geometry for image capture is not determined by the system, such as with tomosynthesis systems using rigid C-arm fixtures that fix the position of source and detector with respect to each other. This geometry typically differs from one exam to the next.

Nor is it feasible to perform separate geometric calibration measurements for each exam. Calibration metrics must be extracted from the image data itself so that this data can be used for tomosynthesis reconstruction.

FIGS. 16-17 given previously outlined some of the geometric considerations for calibration of the source/detector space. Factors that play a part in geometric calibration include position and angular orientation of the detector, including skew and declination, the source-detector distance SID, and position of the source as it transits along a path. Known consistency of the data by accurate geometric calibration improves the results of image reconstruction accordingly.

Consider two images from the tomosynthesis study. It is known that consistency relationships can be formulated utilizing the imaging geometry, based upon the positions of the sources and the detector. Ideally, the method works best when the imaged object is completely contained in both images, otherwise inconsistencies can occur due to object truncation within the image. There are approaches to minimize the impact of truncation, however, improvements are still needed. In effect, these methods use global properties of the images.

Reference is hereby made to U.S. Pat. No. 7,031,497 (Trajkovic) entitled "METHOD FOR COMPUTING OPTICAL FLOW UNDER THE EPIPOLAR CONSTRAINT", incorporated herein in its entirety.

Embodiments of the present disclosure use the epipolar geometry techniques to provide a reference framework for geometric calibration. In order to calculate the epipolar geometry, this method first generates a vector field, using points or features common to members of the set of acquired projection images. This vector field effectively relates shifts in pixel locations for identified features within the image. Metrics characterizing the predominant direction of the vectors in the vector field provide some level of information on the relative orientation of the detector to the source position.

Figure 21B:
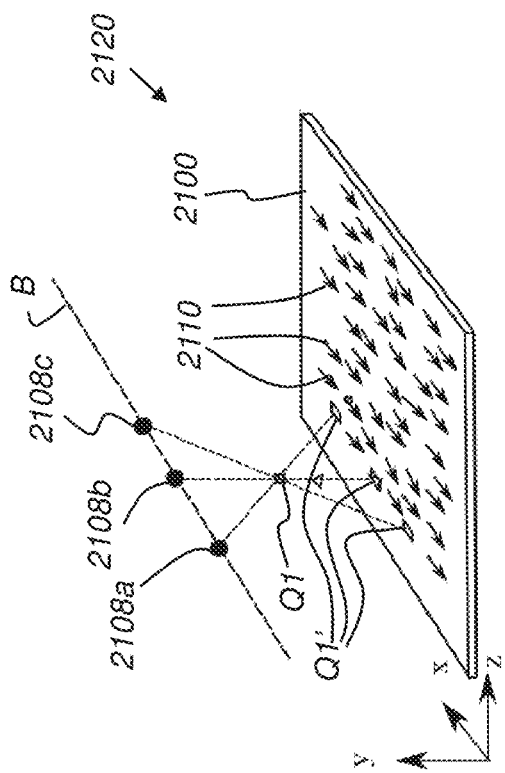
FIGS. 21A and 21B show, in exaggerated form, how feature movement vectors can be generated for tomosynthesis images acquired along an image plane.
Figure 21A:
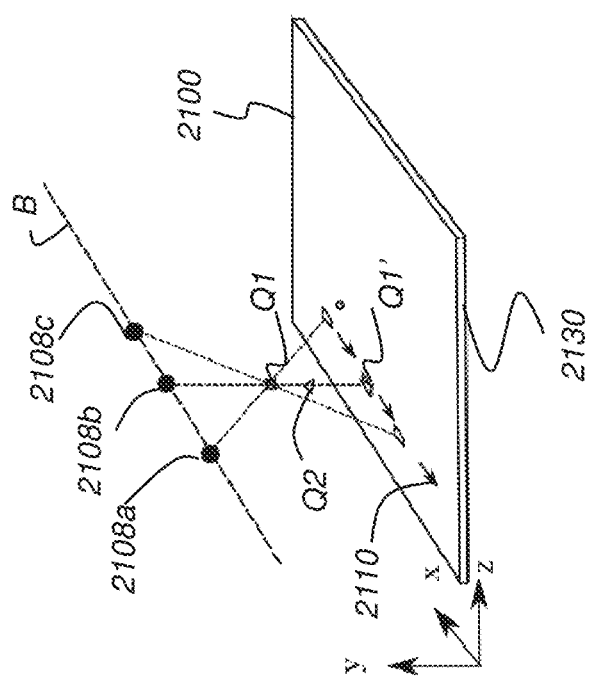

The schematic diagrams of FIGS. 21A and 21B show, in exaggerated form for illustrative purposes, how feature movement vectors 2110 can be generated for tomosynthesis images acquired along an image plane 2100 of a detector 2130. Exemplary x, y, z coordinates are shown. X-ray sources 2108*a*, 2108*b*, and 2108*c* can represent either individual x-ray sources from an array of sources or representative positions of a single x-ray source translated over a track, acquiring an image at each of a number of defined intervals over a source travel path. A linear path is shown; a curved path could alternately be used. An object feature point Q1 is imaged to form an image Q1' as shown in FIG. 21A, with the x-ray source at multiple locations. The resulting shift of points and features, shown for point Q1' in FIG. 21A and for multiple feature points in FIG. 21B, for corresponding features in the image content, generates a vector field 2120, a collection of vectors 2110 that indicate the relative movement of the identified feature points of the imaged object (the patient) corresponding to the different positions of the X-ray sources.

The vectors in the generated vector field can be accurate where object features are unambiguous and the image capture geometry is well defined. However, these methods can be insensitive to other geometric properties, such as movement vectors in different directions caused by the declination of the detector relative to the path traveled by the source. Because of this and other ambiguities, feature tracking can generate a "noisy" vector field, compromising confidence in consequent geometric calculations that are obtained. Even when the source/detector path is relatively well ordered, there can be cases where feature direction alone can be misleading. Where imaged objects are irregular in shape, for example, feature movement vectors may not be uniformly in parallel.

Epipolar geometry, corresponding to the x-ray source and detector positions, can be derived from the vector field for points and features. The generation of epipolar geometry and some key structures and concepts are illustrated in schematic representation in the sequence of perspective views in FIGS. 22A through 22G. To begin the sequence, FIG. 22A shows a detector and three exemplary points in space that are part of the imaged subject, feature points Q1, Q2, and Q3. An image plane 2100 includes the detector and continues beyond the bounds of the detector.

Figure 22B:
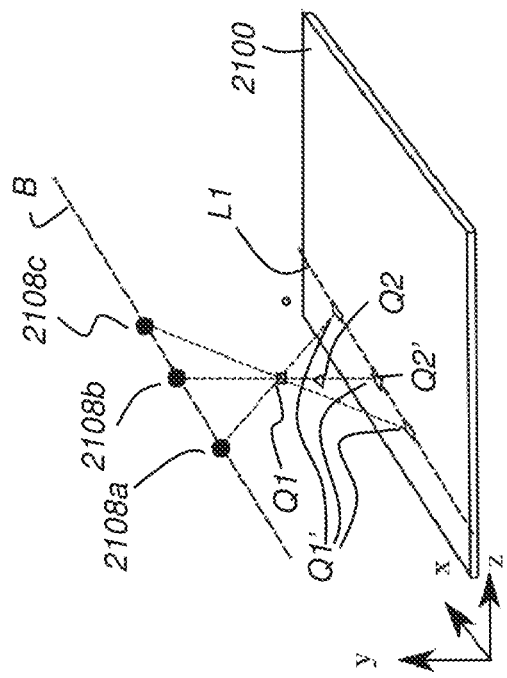
FIGS. 22B and 22C show imaging of features along an epipolar line.
Figure 22A:
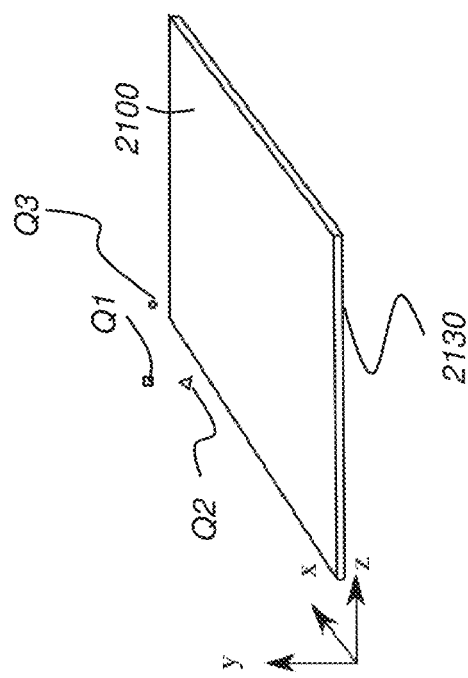
FIG. 22A shows point positions for features in object space that are used to describe epipolar geometry in the description that follows.

FIG. 22B shows schematically the relative path of the X-ray source along a linear scan path, baseline B, during the tomosynthesis scan. For each of three points of the scan, shown as x-ray sources 2108*a*. 2108*b*, and 2108*c*, the system forms an image of point Q1 at corresponding detector pixels Q1'. The two features Q1 and Q2 are aligned along the image plane 2100, aligned with respect to a single point Q1' when irradiated from x-ray source 2108*b*. At each position of x-ray source 2108*a*. 2108*b*, 2108*c* along the scan path of baseline B, the imaged pixel at point Q1', corresponding to feature Q1, shifts along a line L1 in image plane 2100.

Figure 22D:
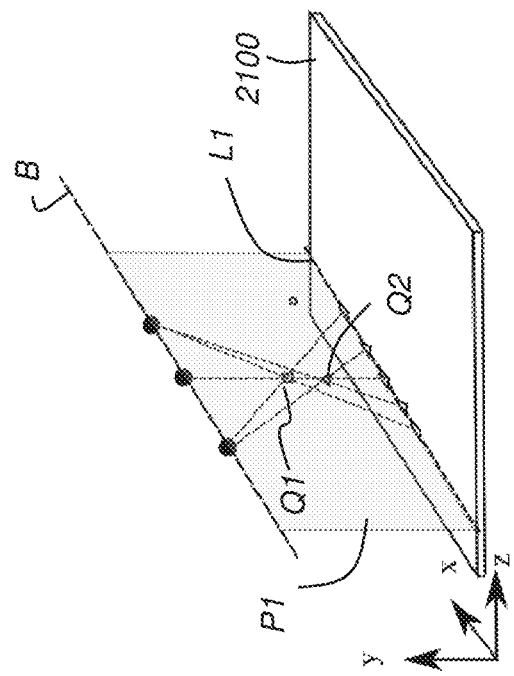
FIG. 22D shows the position of a first plane for features that are imaged along an epipolar line.
Figure 22C:
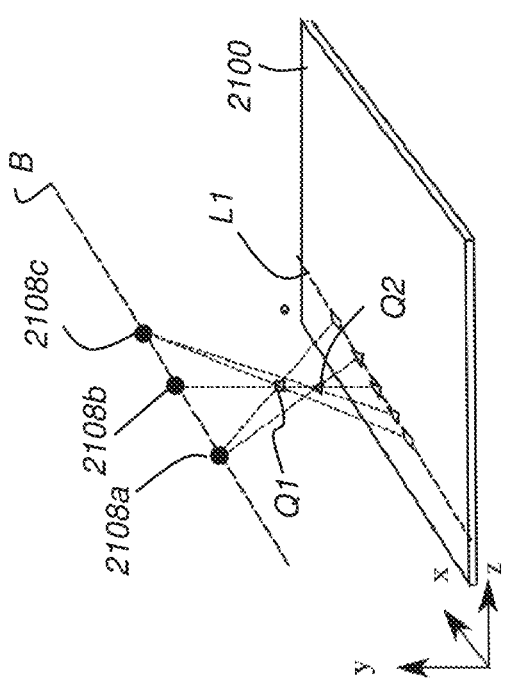

FIGS. 22C and 22D continue the sequence, adding the complexity of further imaging of point Q2 for the same three locations of the x-ray source along the baseline B. Not only do points Q2 and Q1 align with respect to one of the source positions, all imaged points Q2' from point Q2 are also on line L1. A plane P1 can be defined for all points in the imaged subject, such as points Q1 and Q2, that have this alignment relationship. Plane P1 includes the scan path, baseline B, of the x-ray source, as it moves through the positions shown as source 2108*a*-2108*c*, points Q1 and Q2, and line L1 along which any of the corresponding points along plane P1 are imaged. Line L1 on image plane 2100 is an epipolar line on the image plane 2100 of the detector for points Q1, Q2, and all other points lying along plane P1. Baseline B and epipolar line L1 can be considered to define plane P1. Note that point Q3 lies outside of plane P1 and is thus not imaged onto line L1.

Figure 22F:
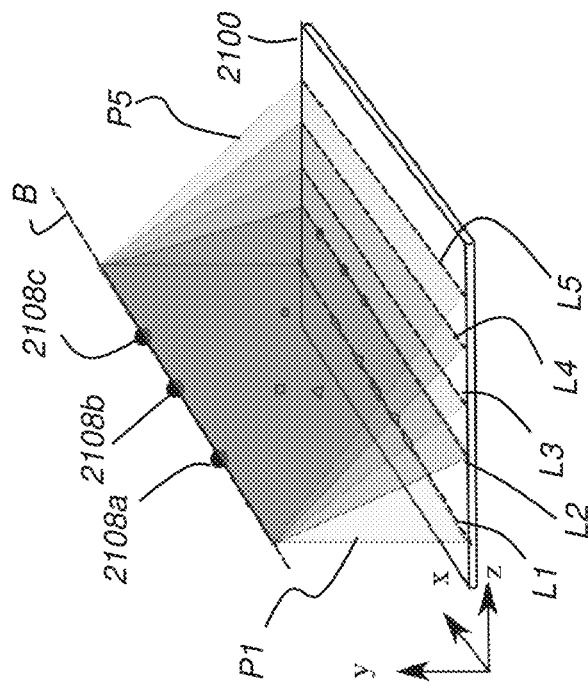
FIG. 22F shows a pencil of planes and corresponding epipolar lines.
Figure 22E:
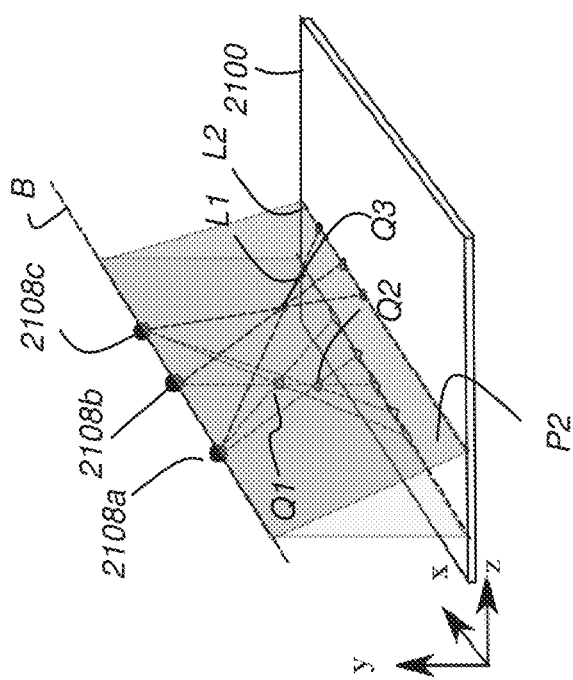
FIG. 22E shows the position of a second plane for features imaged along another epipolar line.

FIG. 22E shows a corresponding relationship that applies for point Q3. Another plane P2 contains point Q3 and all other points that lie in the plane P2 that contains baseline B, the scan path of the x-ray source, and an epipolar line L2 that lies along image plane 2100.

Figure 22G:
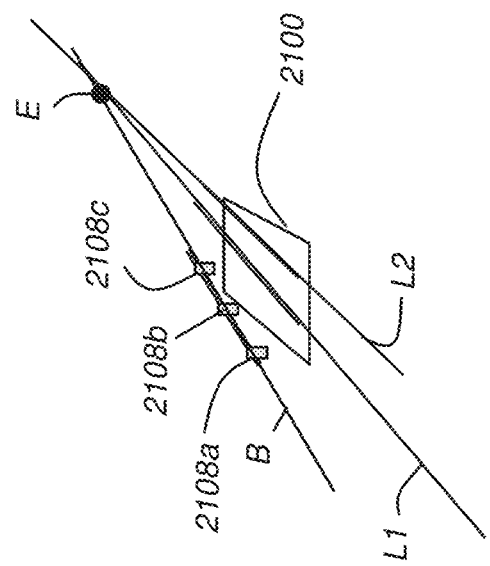
FIG. 22G shows extension of epipolar lines and the baseline to intersect at the epipole.

The same pattern applies for innumerable other points of the imaged subject, so that multiple epipolar lines can be defined along image plane 2100. FIG. 22F shows epipolar lines L1, L2, L3, LA, and L5 with corresponding planes P1 . . . P5 that form a pencil of planes about baseline B. Each plane P1 . . . P5 is defined by baseline B and a corresponding epipolar line. Only a small number of planes are shown; epipolar geometry can be computed with respect to a finite number of such planes as those shown as planes P1 . . . P5.

Where the scan path is perfectly aligned in parallel with the detector surface, epipolar lines are parallel to each other and do not intersect with each other. In practice, because alignment is seldom perfect, the epipolar lines are generally slightly non-parallel and intersect at an epipole. The epipole is in the image plane 2100, but generally spaced apart at some distance from the detector. FIG. 22G shows, at greatly reduced scale and in exaggerated form, an epipole E at the intersection of epipolar lines L1, L2 and other epipolar lines; at epipole E, the epipolar lines intersect with each other and also intersect with the extended baseline B, the extended line of travel defined for the x-ray source or sources shown at 2108*a*. 2108*b*, and 2108*c*. In geometric terms, a "pencil" of lines intersect at epipole E.

At the pixel level, feature movement can be tracked along epipolar lines, as described with reference to FIGS. 22A-22G. In obtaining projection images, the amount of relative movement of the x-ray source from a position n to a position (n+1) is determined by the imaging apparatus itself, as described previously with relation to FIG. 12 (or, correspondingly, for an array in FIG. 13). Knowing the location of the epipole provides the system with a number of parameters that characterize relative movement of the x-ray source over the image plane, including skew, pitch, and x-y coordinate position. The information provided by the epipolar geometry, however, does not by itself provide sufficient information for determining the source-to-image distance.

Using the tools of epipolar geometry, the spatial relationship of each image to the succession of images can be determined by a Fundamental Matrix F that applies for every pair of corresponding points x and x', wherein x and x' are two image points representing the same object feature point:

$$x'^T F x = 0$$

In the above equation, superscript T indicates the transpose of the coordinate matrix for point x'. Fx describes the epipolar line corresponding to both image points x and x'.

Methods for calculating the Fundamental Matrix using the changed positions of specific points or line segments of an image are known. These calculations can be used to predict, as well as to verify, point movement from one projection image acquisition n (with the x-ray source at a first position) to the next projection image acquisition (n+1) (with the x-ray source shifted to a second position).

Given this basic understanding of the feature tracking and epipolar geometry methods derived from a vector field, it can be seen that they represent different approaches to the computational problem of tracking point-by-point movement of pixel content (or, alternately, of tracking imaged feature points) between successive images. Each framework for describing relative movement of source or detector along the imaging path has particular strengths and limitations.

In order to provide baseline data for system calibration, the proposed method of the present disclosure utilizes epipolar geometry derived from feature or point movement for acquired image content from the tomosynthesis images. The movement vector field can be reduced, using epipolar correspondence and optimization techniques, so that only vectors that show a strong likelihood of being significant are used for calibration data. The epipolar geometry arguments indicate that if the position of an epipole can be assumed, then a vector field can be generated from the image content, wherein the generated vector field correlates with the vector field produced according to feature movement.

Figure 23A:
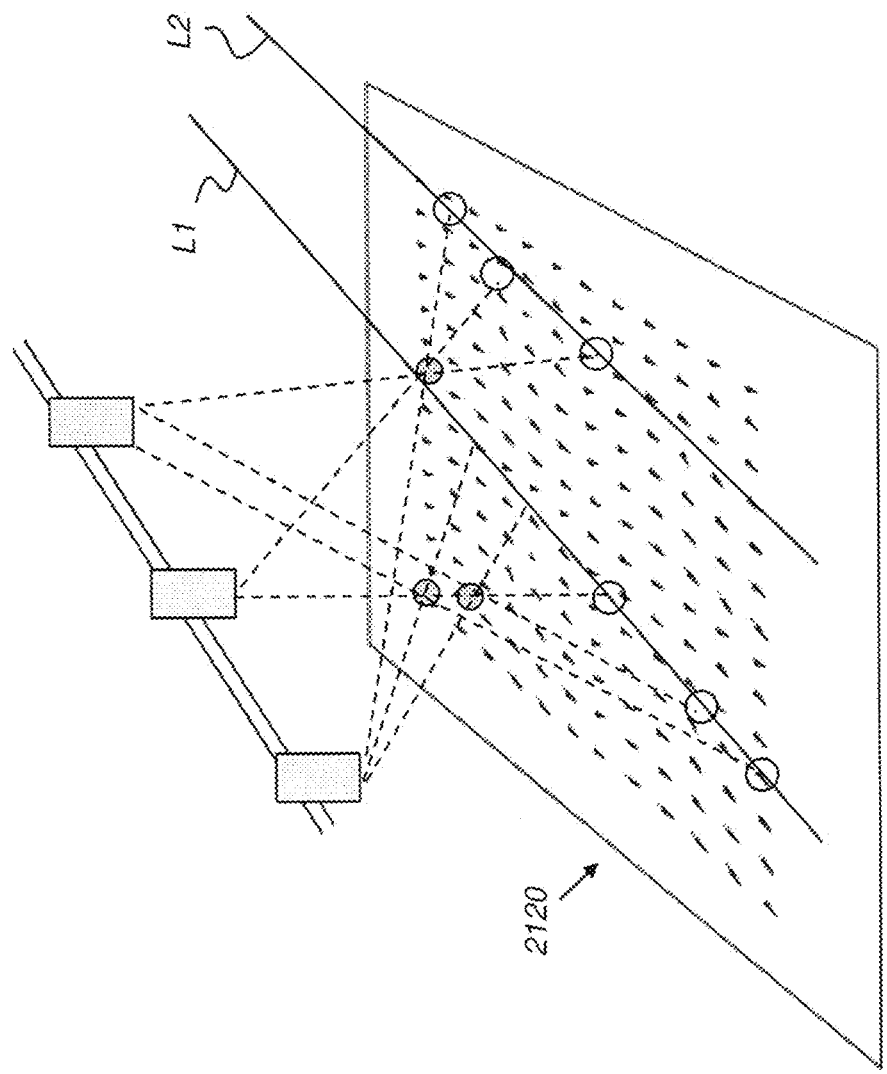
FIG. 23A shows a vector field with a number of overlaid epipolar lines.
Figure 23B:
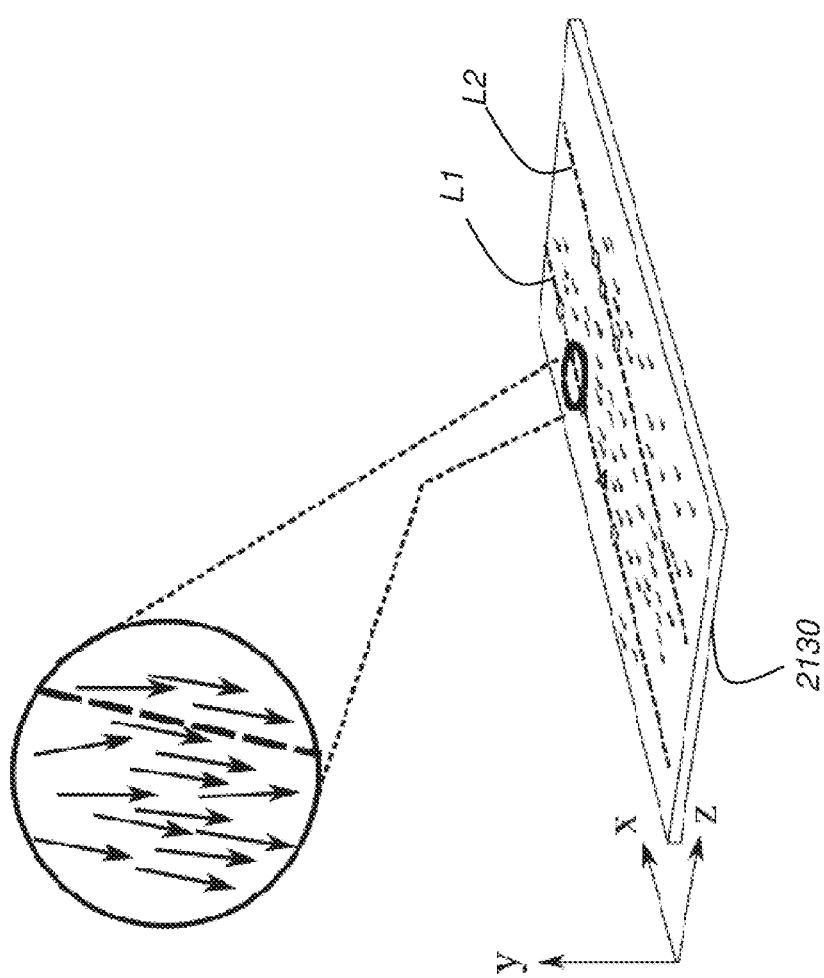
FIG. 23B shows the geometric relation between an epipolar line and nearby vectors.

FIGS. 23A and 23B show, in simplified schematic form, epipolar lines L1, L2 overlaid onto an exemplary vector field 2120. The epipolar lines L1, L2, . . . can be considered as consisting of unit vectors aligned along the corresponding epipolar lines. The correspondence of feature movement vectors with unit vectors from the epipolar geometry can then provide a measure of the relative "correctness" of vectors used for determining relative source position in subsequent calculation. Using this metric, only those movement vectors that are judged most reliable are retained and used.

Similarly, the epipolar vector field appears to be a set of unit vectors radially emanating from the position of the proposed epipole. The epipole itself may be in the imaged area, but is likely to lie outside the imaged area along the extended image plane, as was shown schematically in FIG. 22G. A metric A(e) used for calculating the source-detector geometry can be generated by accumulating dot product results between the corresponding vectors over the epipolar vector field and the vector field based on feature or point movement as in the following equation:

$$A(e) = \sum_{i=1}^{n} ft(\vec{i}) \cdot epi(\vec{i})$$

Wherein ft(i) are the feature or point vectors and epi(i) are the associated epipolar vectors for each of n positions, corresponding to n projection images. The generalized dot product for two vectors a and b is computed $$a \cdot b = a \|a\| \|b\| \cos \theta$$

wherein notation $\| \ \|$ indicates vector magnitude and $\theta$ is the angle between the vectors. The dot product of two vectors that are parallel is at a maximum value, based on vector length (for unit vectors, value 1.0).

At its calculated value. A(e) indicates how well the vector field correlates with epipolar geometry. Once the optimal epipole is located, system calculations can then identify characteristics such as skew of the source path relative to the detector, declination of the source path relative to the plane of the detector, and spatial location of the detector relative to the sources, but without precise identification of the source-detector distance. This information can help to calibrate the portable tomosynthesis or tomographic system for a pair of tomographic images.

Optimization and Model Selection

According to an embodiment of the present disclosure, a method for source-detector calibration of a mobile radiography apparatus employs a mathematical optimization as a vehicle for matching one of a set of epipolar geometry models to feature or point movement data in the series of acquired projection images.

For this embodiment, one of a number of possible epipolar geometry models can be set up according to probable spatial arrangements of the x-ray source and detector. The models can differ from each other according to features such as skew relative to the detector pixel array, pitch of the source travel path, and epipole position within the image plane, considering the unbounded image plane extended outward beyond the edges of the digital detector. Multiple epipolar geometry models can be parametric models, generated according to points in space along the x-ray source path for example. Alternately epipolar models can be calculated separately beforehand, stored in a library that provides a database of epipolar geometry models that can be used directly or appropriately adapted as needed for calibration in a particular tomosynthesis imaging exam. Optionally, an epipolar geometry model can be generated based on data obtained from the image series, then refined as processing proceeds.

Referring to the logic flow diagram of FIG. 24, the mobile radiography apparatus acquires a series of tomosynthesis projection images in an acquisition step S2410. A vector field is generated in a vector field generation step S2420, wherein each vector is indicative of feature movement between picture elements of two successive projection images in the acquired series. In a looping sequence, an epipolar model selection step S2430 obtains or generates an epipolar geometry model as a candidate, such as from a set of epipolar models that are suitable for the mobile radiography apparatus or calculated from given parameter data.

Epipolar models can differ from each other, for example, in terms of relative position of the epipole with respect to the image plane geometry; this relationship defines the relative orientation and positioning of epipolar planes for the source-detector geometry, as described previously with reference to FIGS. 22A-22G. A dot product calculation step S2440 then performs a series of dot product (scalar product) calculations that indicate how closely the measured data approximates model data for the candidate model. A decision step S2450 determines whether the computed values are close enough for selection or modification of the candidate epipolar model and whether or not another model should be generated or selected, returning processing to step S2430 as needed. When a suitable model has been selected, a calibration step S2460 can then be executed in order to calibrate the source-detector path for the acquired set of projection images.

According to an embodiment of the present disclosure, the goal of the optimization for model selection in step S2430 or adaptation, and for subsequent source-detector calibration is to optimize an energy relationship, such as the following:

$$E = 1/2 \Sigma (1 - V_x(x,y) \cdot \overline{V_x})^2 + (1 - V_y(x,y) \cdot \overline{V_y})^2$$

wherein:
E is the energy value to be optimized (generally maximized or minimized);
$V_x(x,y)$ and $V_y(x,y)$ are measured values;
$\overline{V_x}$ and $\overline{V_y}$ are values calculated from the model;
This relationship is derived from the generalized mathematical concept of energy calculation, more abstractly defined as the integral, over a finite interval, of the square of a function representing signal content. Iterative calculation can be used to refine and improve the energy relationship until a suitable level of optimization is achieved.

Calibrating Source and Detector Positions

Figure 25A:
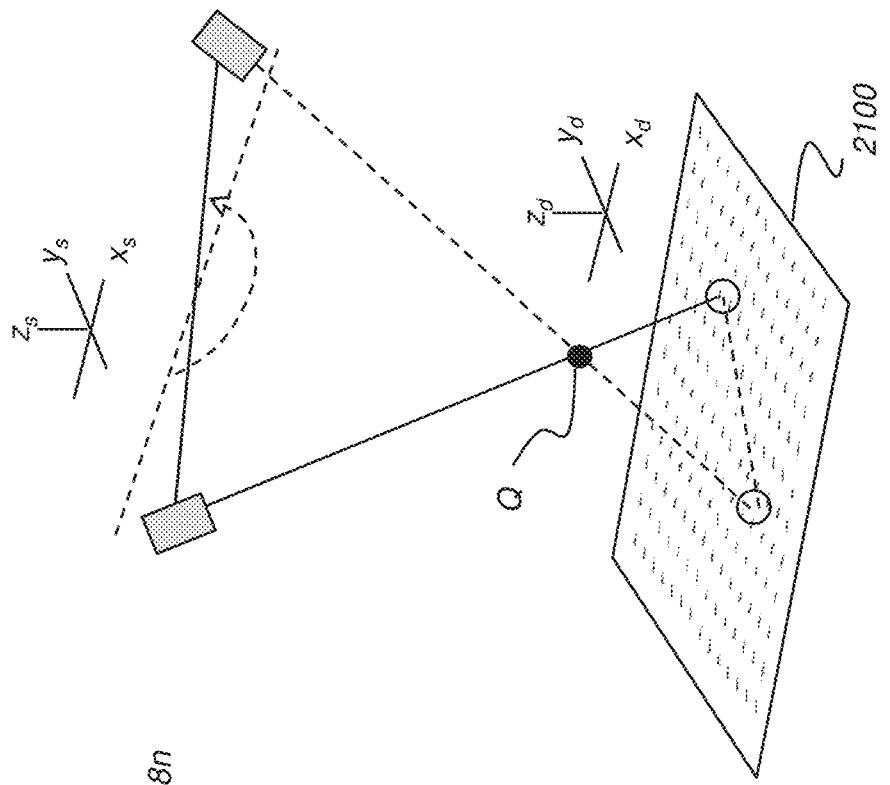
FIGS. 25A and 25B are schematic diagrams showing some of the geometric considerations for calibration and skew correction when using a portable radiographic imaging apparatus for tomosynthesis.
Figure 25B:
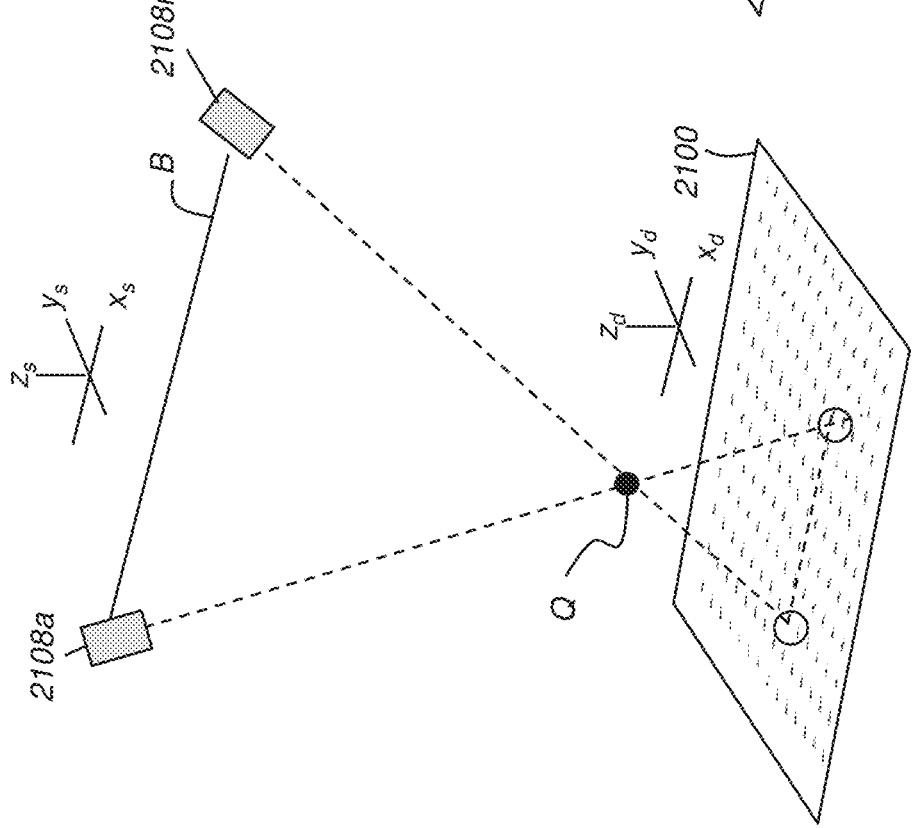

The goal of source/detector calibration is to identify geometric factors of relative positioning of components in the image path, wherein their relative position affects image reconstruction. FIGS. 25A and 25B show some of the geometric considerations for calibration when using a portable radiographic imaging apparatus for tomosynthesis. The coordinate space for source position is shown along ($x_s$, $y_s$, $z_s$) axes. The image plane 2100 that includes the detector is shown in a coordinate space having ($x_d$, $y_d$, $z_d$) axes.

Whether there is source movement or an array of sources, the x-ray source appears, from the perspective of the detector image plane 2100, to move from source 2108a position along baseline B to source 2108n position. At the same time, the image of a feature point Q moves through corresponding image plane positions, from a first pixel to a second pixel. The two-dimensional information for movement within source position and coordinate space allows a measurement of skew. The relative height of feature point Q with respect to source-detector distance can be readily determined using similar-triangles. It is possible to calculate source-detector distance where the height of feature point Q relative to the image plane 2100 is known, such as through use of a radio-opaque marker of known height, positioned on the image path between detector and source, on or near the patient, for example.

The position of the x-ray source along the translation path of baseline B can be calculated and verified from image data at image plane 2100 using the epipolar and image vector data described previously. It should be noted that skew of the baseline B relative to the image plane 2100 coordinate space, represented in FIG. 25B as rotation with respect to the z axis, must be quantified for accurate calibration. Relative pitch of baseline B, corresponding to an angle within the x-z plane in the coordinate space shown in FIG. 25B, is less significant and can be ignored in some tomosynthesis applications. Pitch can also be calculated using multiple images having an identified feature point Q and using the epipolar geometry obtained as described herein. In this way, an accurate mapping of the coordinate spaces can be obtained in order to properly determine geometric features for calibration.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for geometric calibration of a mobile radiography apparatus having an x-ray source, the method executed at least in part by a computer, comprising:
   calculating an x-ray source path;
   calculating a pitch of the x-ray source path:
   acquiring a series of tomosynthesis projection images of a patient positioned between the x-ray source and a detector positionally uncoupled from the x-ray source, the series including a first and second acquired projection image;
   generating a vector field having a first set of vectors indicative of feature movement between the first and second acquired projection images;
   generating an associated model epipolar geometry by associating the generated vector field with an epipolar geometry according to an optimization of an energy relationship between an epipolar model and the generated vector field;
   calibrating the mobile radiography apparatus according to the associated model epipolar geometry;
   reconstructing at least a portion of one of the acquired tomosynthesis projection images according to the calibration; and
   displaying, on a display, the reconstructed tomosynthesis projection image.

2. The method of claim 1 wherein the optimization of the energy relationship is determined by computing dot product calculations between the first set of vectors and vector data from the model epipolar geometry.

3. The method of claim 1 wherein acquiring the series of tomosynthesis projection images includes translating the x-ray source along the x-ray source path.

4. The method of claim 1 wherein acquiring the series of tomosynthesis projection images includes using an array of x-ray sources.

5. The method of claim 1 further comprising normalizing the first set of vectors to unit vectors.

6. A method for geometric source-detector calibration of a mobile radiography apparatus having an x-ray source, the method executed at least in part by a computer, comprising:
- calculating an x-ray source path;
- calculating a pitch of the x-ray source path:
- acquiring a series of tomosynthesis projection images of a patient using a detector positioned behind the patient relative to the x-ray source, the detector being mechanically uncoupled from the x-ray source, the series including a first and second acquired projection image;
- generating a vector field having a first set of unit vectors indicative of an image feature movement between the first and second acquired projection images;
- calculating an epipolar geometry for the acquired series of tomosynthesis projection images according to the vector field;
- calibrating the x-ray source path to an image plane according to the calculated epipolar geometry;
- reconstructing at least a portion of one of the acquired tomosynthesis images according to the calibrated x-ray source path; and
- displaying, on a display, the reconstructed tomosynthesis projection image.

7. The method of claim 6 wherein generating the vector field is accomplished using a set of image features.

8. The method of claim 6 wherein calculating an epipolar geometry includes calculating a spatial location of an epipole disposed outside of the image plane.

9. A method for geometric calibration of a mobile radiography apparatus having an x-ray source, the method executed at least in part by a computer, comprising:
- calculating an x-ray source path;
- calculating a pitch of the x-ray source path:
- moving the x-ray source along the x-ray source path to acquire a series of tomosynthesis projection images of a patient on a digital detector positioned behind the patient relative to the x-ray source, the series including a first acquired projection image acquired at a first x-ray source position and a second acquired projection image acquired at a second x-ray source position;
- generating a vector field having a first set of vectors indicative of feature movement between the first and second acquired projection images;
- calculating a spatial location of an epipole according to the generated vector field;
- calculating a source-to-detector distance according to (i) the epipole spatial location, (ii) a difference between the first and second x-ray source positions, and (iii) a relative movement distance of an image feature between at least two acquired projection images;
- calibrating the x-ray source path to the detector according to the calculated source-to-detector distance; and
- reconstructing at least a portion of one of the acquired tomosynthesis projection images according to the calibrated x-ray source path; and
- displaying, on a display, the reconstructed tomosynthesis projection image.

10. The method of claim 9 further comprising calculating a skew between the x-ray source path and the detector.

11. The method of claim 9 wherein calculating the source-to-detector distance comprises using a marker positioned in the x-ray source path.

* * * * *

UNITED STATES PATENT AND TRADEMARK OFFICE
CERTIFICATE OF CORRECTION

PATENT NO. : 10,631,818 B2
APPLICATION NO. : 16/028935
DATED : April 28, 2020
INVENTOR(S) : Vogelsang et al.

It is certified that error appears in the above-identified patent and that said Letters Patent is hereby corrected as shown below:

In the Specification

Column 16, Line 20   Please replace "$a \cdot b = a\|a\|\|b\|\cos \Theta$" with $-- a \cdot b = \|a\| \|b\| \cos \theta --$ Column 17, Line 25   Please replace "$E = 1/2 \Sigma (1 - V_x(x,y) \cdot \overline{V_x})^2 + (1 - V_y(x,y) \cdot \overline{V_y})^2$"
with $-- E = \frac{1}{2} \sum (1 - V_x(x,y) \cdot \overline{V_x})^2 + (1 - V_y(x,y) \cdot \overline{V_y})^2 --$ Signed and Sealed this
First Day of September, 2020

Andrei Iancu
*Director of the United States Patent and Trademark Office*